> # (12) United States Patent
> Tsuji et al.

(10) Patent No.: US 9,877,474 B2
(45) Date of Patent: Jan. 30, 2018

(54) METHOD FOR MAINTAINING ORGAN OR TISSUE FOR TRANSPLANTATION USE FOR LONG PERIOD

(71) Applicant: Organ Technologies, Inc., Minato-ku, Tokyo (JP)

(72) Inventors: Takashi Tsuji, Nagareyama (JP); Masamitsu Oshima, Noda (JP)

(73) Assignee: Organ Technologies, Inc., Minato-ku, Tokyo (JP)

( * ) Notice: Subject to any disclaimer, the term of this patent is extended or adjusted under 35 U.S.C. 154(b) by 0 days.

(21) Appl. No.: 14/426,011

(22) PCT Filed: Aug. 29, 2013

(86) PCT No.: PCT/JP2013/073207
§ 371 (c)(1),
(2) Date: Mar. 4, 2015

(87) PCT Pub. No.: WO2014/038473
PCT Pub. Date: Mar. 13, 2014

(65) Prior Publication Data
US 2015/0289499 A1  Oct. 15, 2015

(30) Foreign Application Priority Data
Sep. 8, 2012 (JP) ................... 2012-197986

(51) Int. Cl.
*A01N 1/02* (2006.01)
(52) U.S. Cl.
CPC ......... *A01N 1/0226* (2013.01); *A01N 1/0247* (2013.01)
(58) Field of Classification Search
CPC ....................................................... A01N 1/00
See application file for complete search history.

(56) References Cited

U.S. PATENT DOCUMENTS

| 7,410,474 | B1 | 8/2008 | Friend et al. | |
|---|---|---|---|---|
| 2002/0012988 | A1* | 1/2002 | Brasile | A01N 1/0247 435/1.2 |
| 2008/0017194 | A1* | 1/2008 | Hassanein | A01N 1/02 128/200.24 |
| 2010/0209902 | A1 | 8/2010 | Zal | |
| 2011/0076666 | A1* | 3/2011 | Brassil | A01N 1/0247 435/1.2 |
| 2012/0330438 | A1* | 12/2012 | Keshavjee | A01N 1/0215 623/23.65 |
| 2013/0017533 | A1* | 1/2013 | Tsuji | A01N 1/0247 435/1.2 |

FOREIGN PATENT DOCUMENTS

| EP | 0376763 | A2 | 7/1990 |
|---|---|---|---|
| JP | 60-061501 | A | 4/1985 |
| JP | 06-016571 | A | 1/1994 |
| JP | 06-305901 | A | 11/1994 |
| JP | 2007167124 | | 7/2007 |
| WO | 1987006836 | A1 | 11/1987 |
| WO | 1997043899 | | 11/1997 |
| WO | 2004105484 | A1 | 9/2004 |
| WO | WO 2011/093268 | * | 8/2011 |
| WO | 2011140241 | A2 | 11/2011 |

OTHER PUBLICATIONS

Eventov-Friedman S. et al.: "Embryonic pig liver, pancreas, and lung as a source for transplantation: Optimal organogenesis without teratoma depends on distinct time windows" Proc. Natl. Acad. Sci., vol. 102, No. 8, pp. 2928-2933.
Fondevila C, et al.: Am. J. Transplant. 12, 2012, pp. 162-170.
Fuchinoue et al., "Hypothermic perfusion preservation and artificial oxygen carrying agents", Low Temp Med, vol. 22, No. 1, 1996, pp. 68-77.
Lechler RI. et al., "Organ transplantation—how much of the promise has been realized?", Nat. Med. 11(6): 605, 2005, pp. 605-613.
Malchesky PS. et al.: Artif. Organs. 30(9): 655, 2006.
Moers C. et al.: N. Engl. J. Med. 360(1): 7, 2009.
Pier Luigi Pilati et al., "Isolated Vascular Perfusion of Human Colon with Adenocarcinoma", World Journal of Surgery, 1999, vol. 23, pp. 197-201.
Yang YG. et al.: Nat. Rev. Immunol. 7(7): 519, 2007.
Ishikawa et al., Hypothermic temperature effects on organ survival and restoration, Scientific Reports, 2015, p. 1-12, 5:9563.
Choladda Vejabhuti Curry, MD, Erythrocyte Count (RBC): Reference Range, Interpretation, Collection and Panels, Medscape, Retrieved from the Internet on Sep. 13, 2017, 1 page.

* cited by examiner

*Primary Examiner* — Ruth Davis
(74) *Attorney, Agent, or Firm* — Dennis A. Bennett

(57) ABSTRACT

The object of the present invention is to provide a technology that enables long-term preservation while maintaining the function of an organ or tissue for transplantation. A further object is utilizing this technology to provide a technology for suppressing tissue disorder accompanying warm ischemia and reperfusion as well as restoring an organ from a cardiac arrest donor to a level compatible for transplantation. A method that employs perfusion by a perfusate etc. is provided, comprising each of the following steps of: (a) connecting a perfusate instream cannula for streaming said perfusate into said "organ or tissue," (b) connecting a perfusate outstream cannula for streaming said perfusate out from said "organ or tissue," and (c) perfusing a perfusate comprising an oxygen carrier and a blood coagulation inhibitor into said organ or tissue.

6 Claims, 22 Drawing Sheets

[Figure 1]
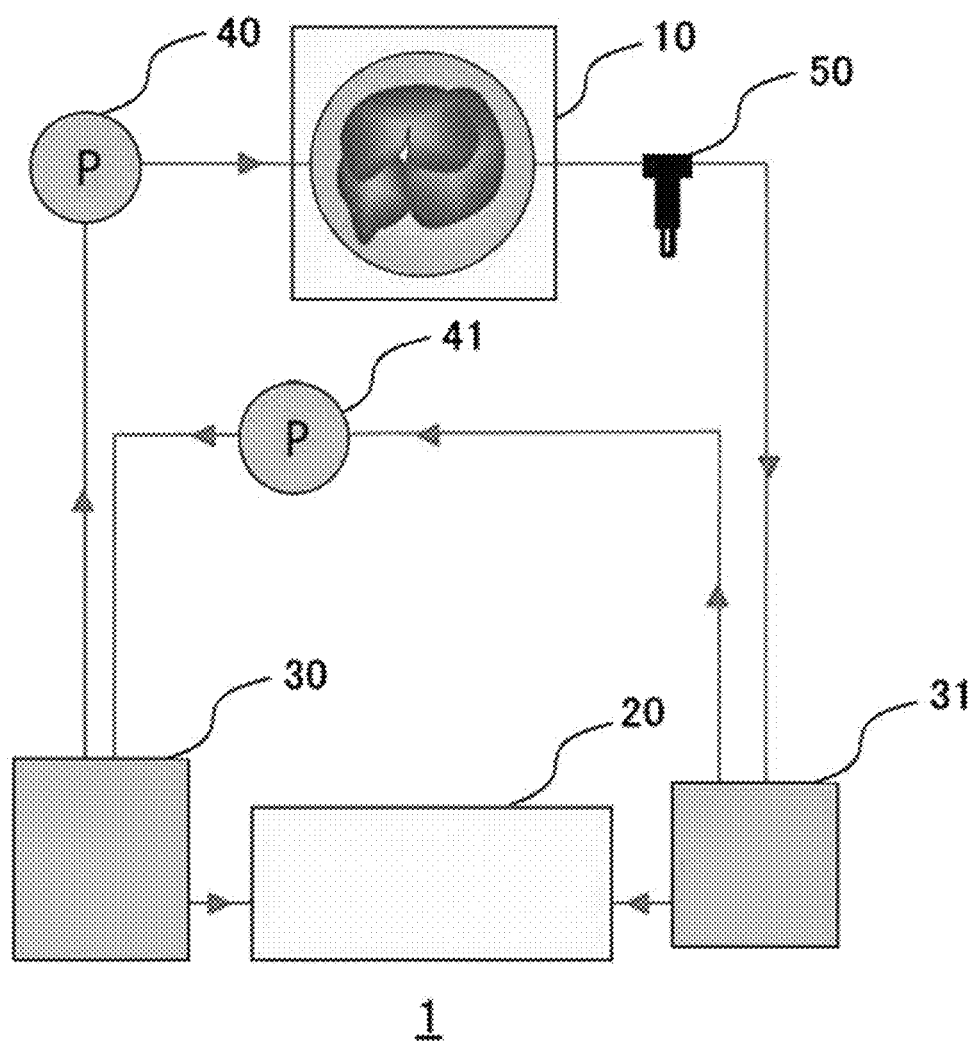

[Figure 2]
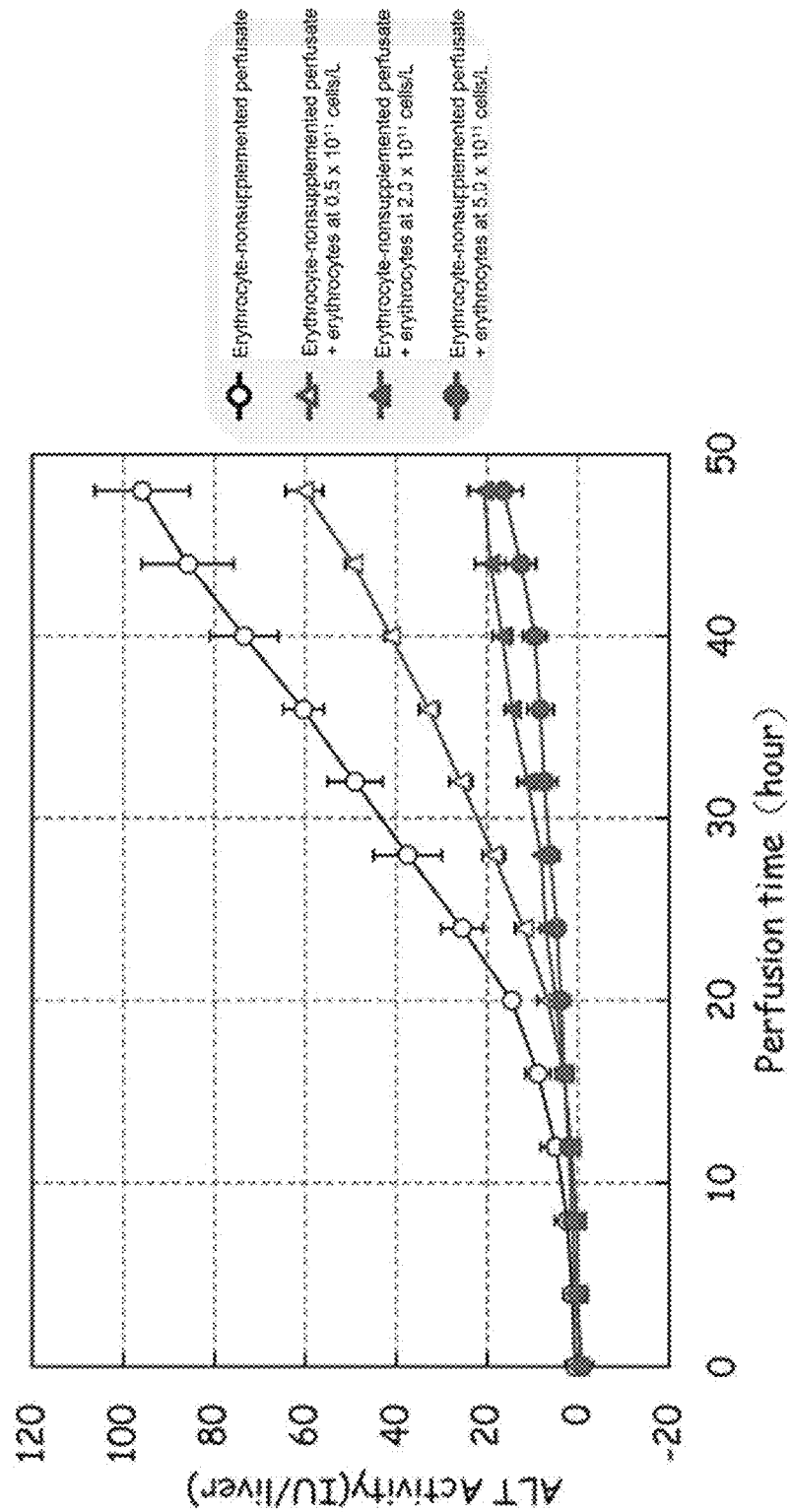

[Figure 3]
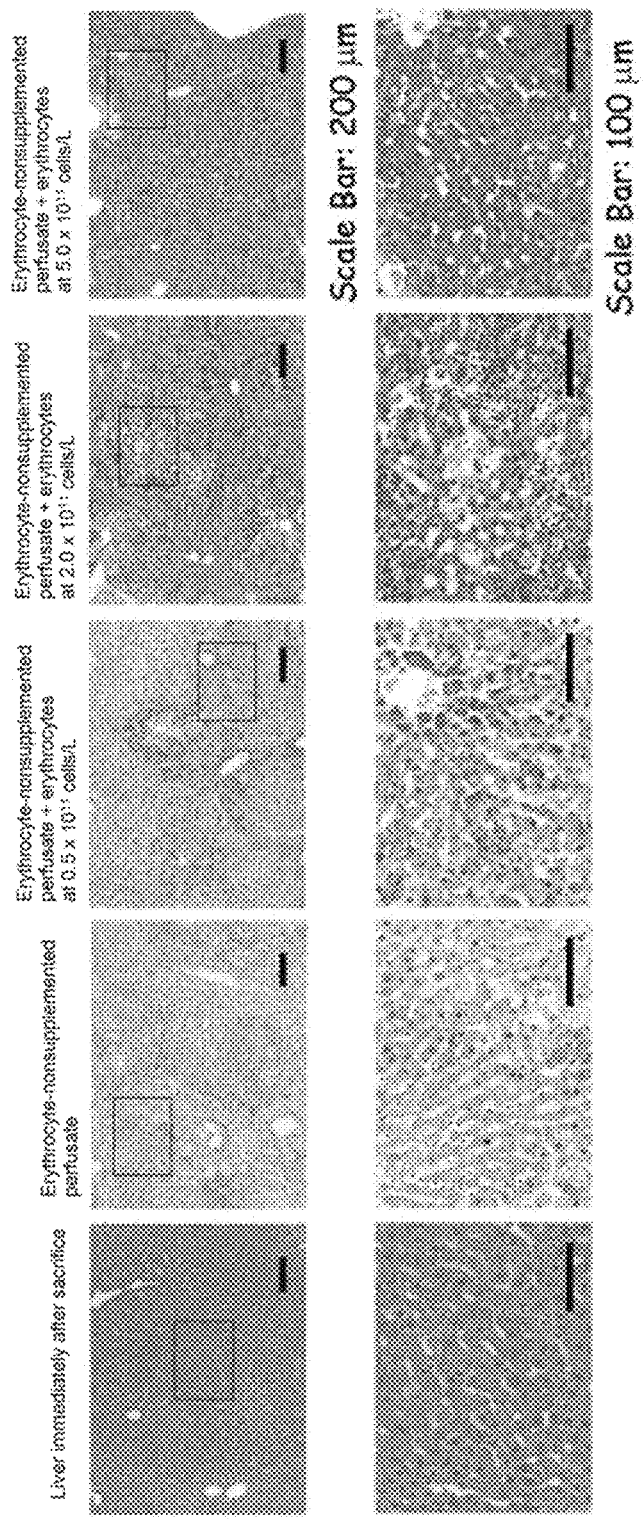

[Figure 4]
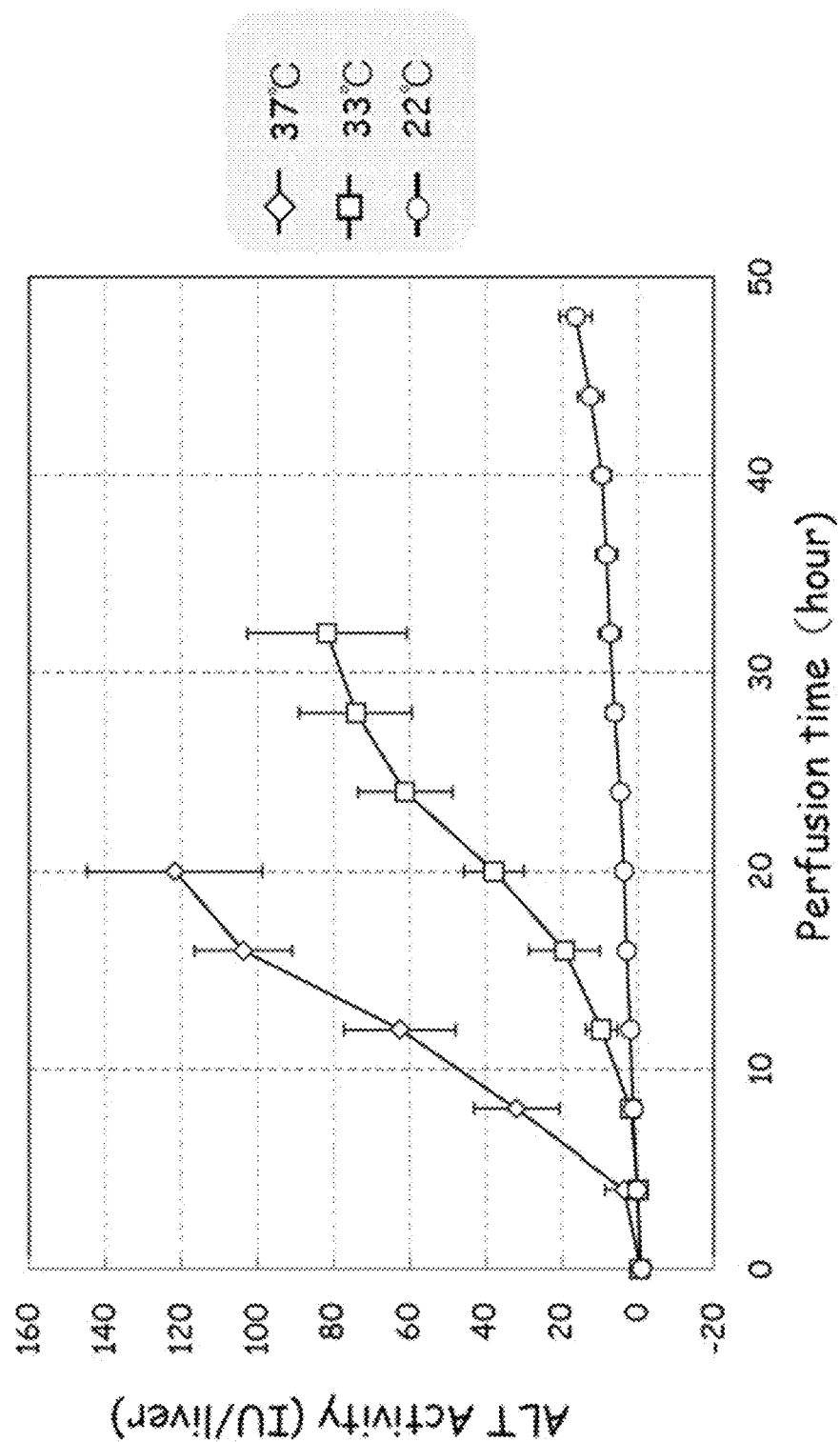

[Figure 5]
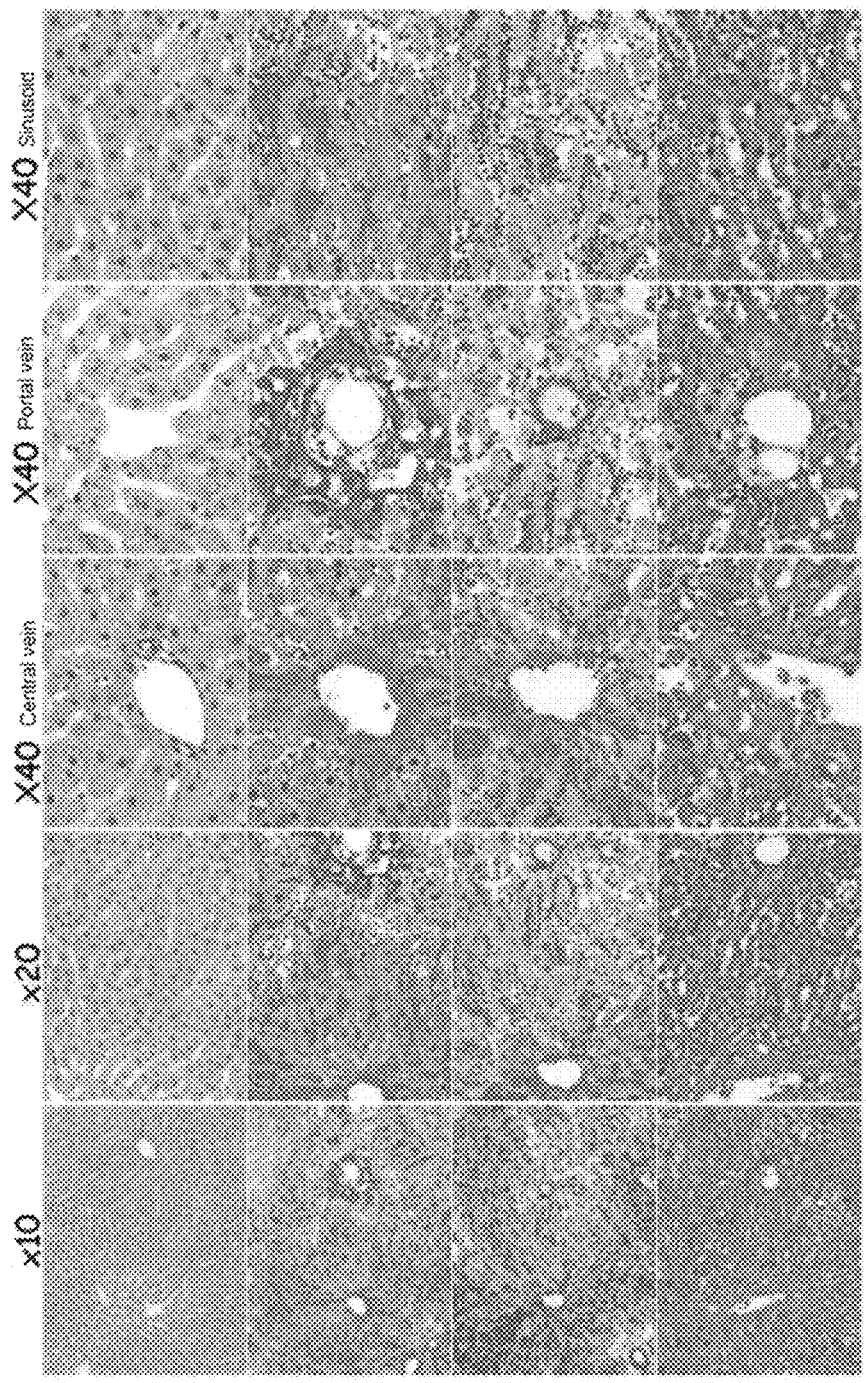

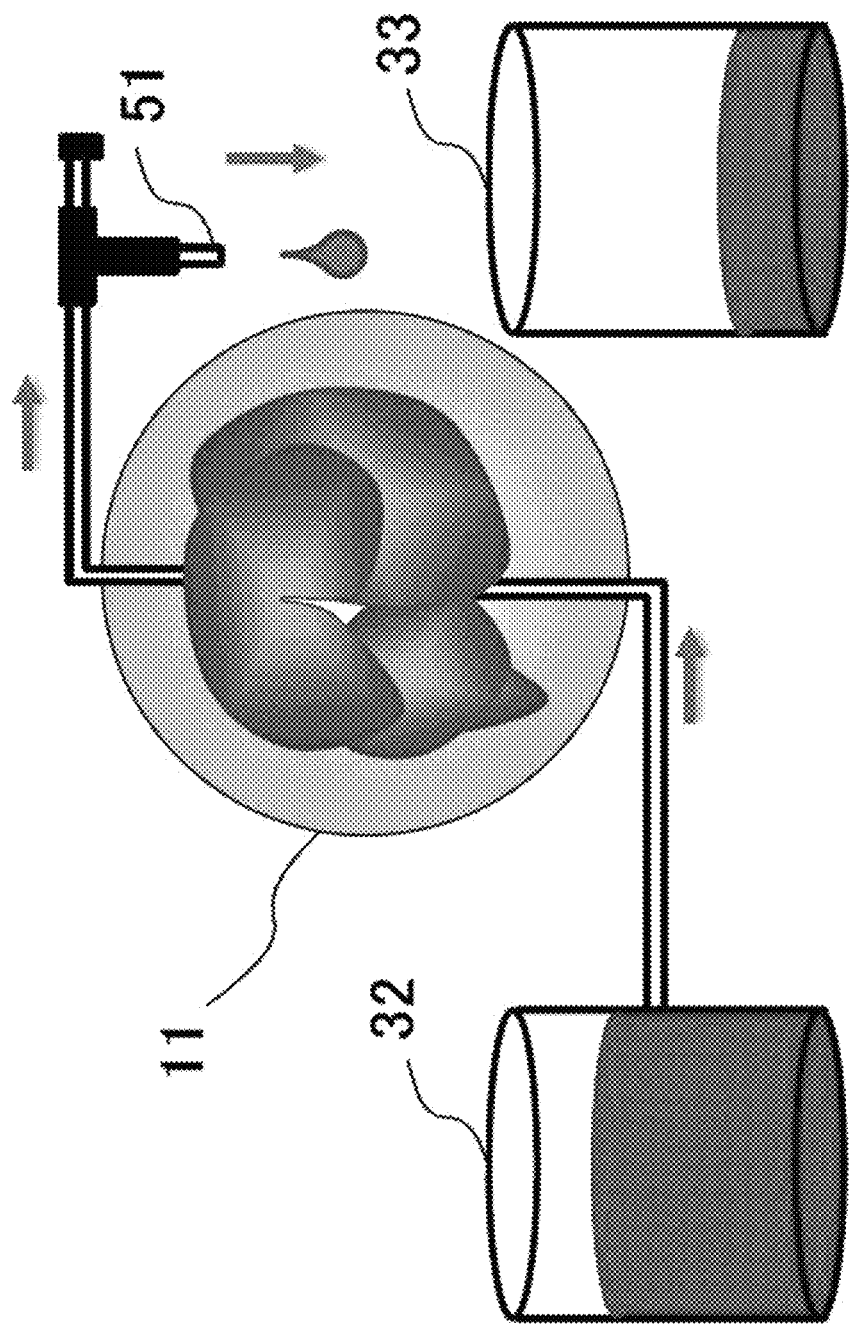
[Figure 6]

[Figure 7]
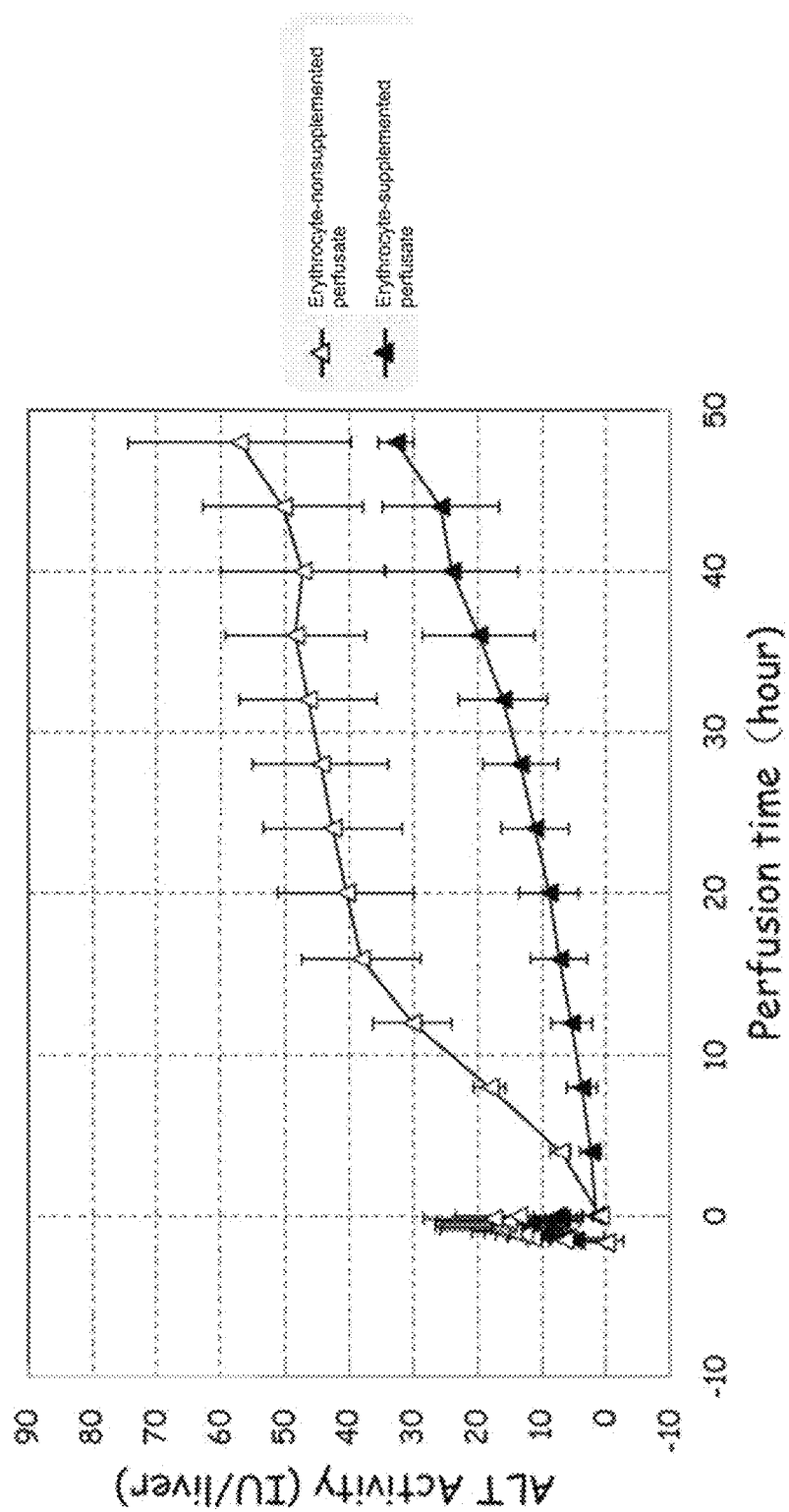

[Figure 8]
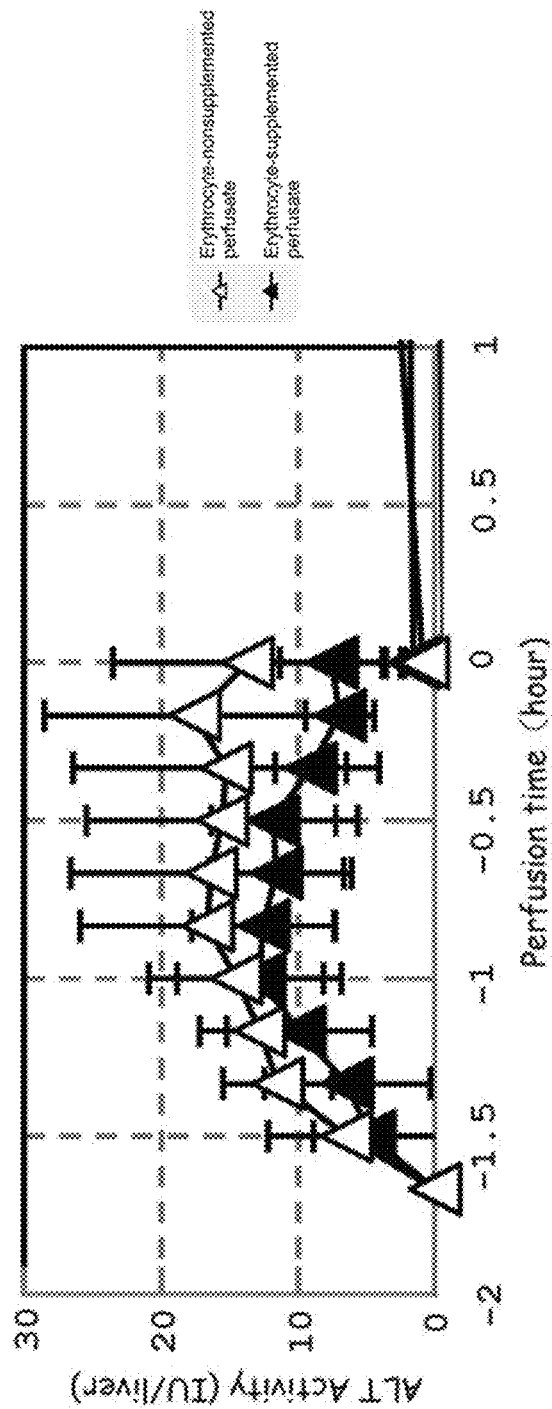

[Figure 9]
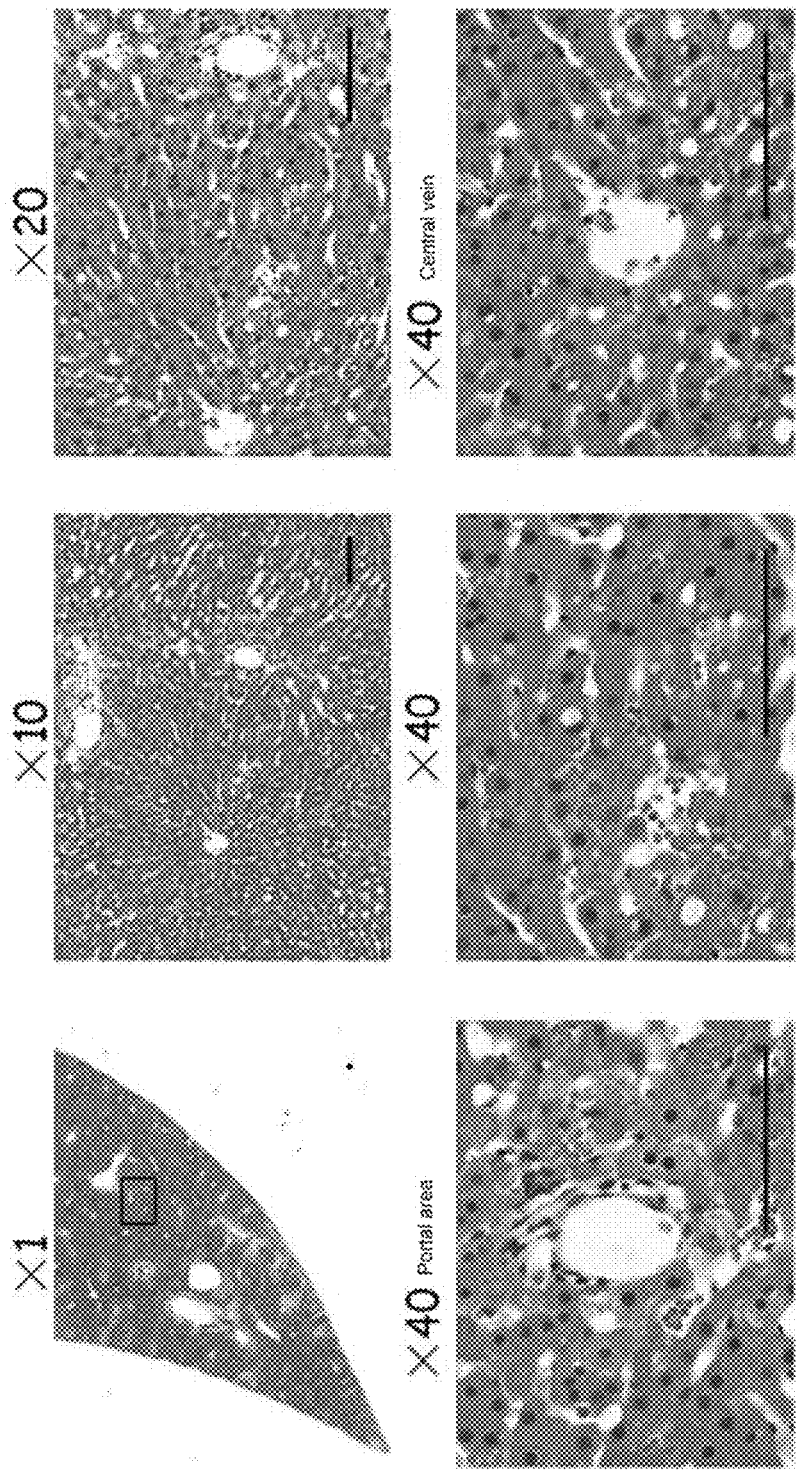

[Figure 10]
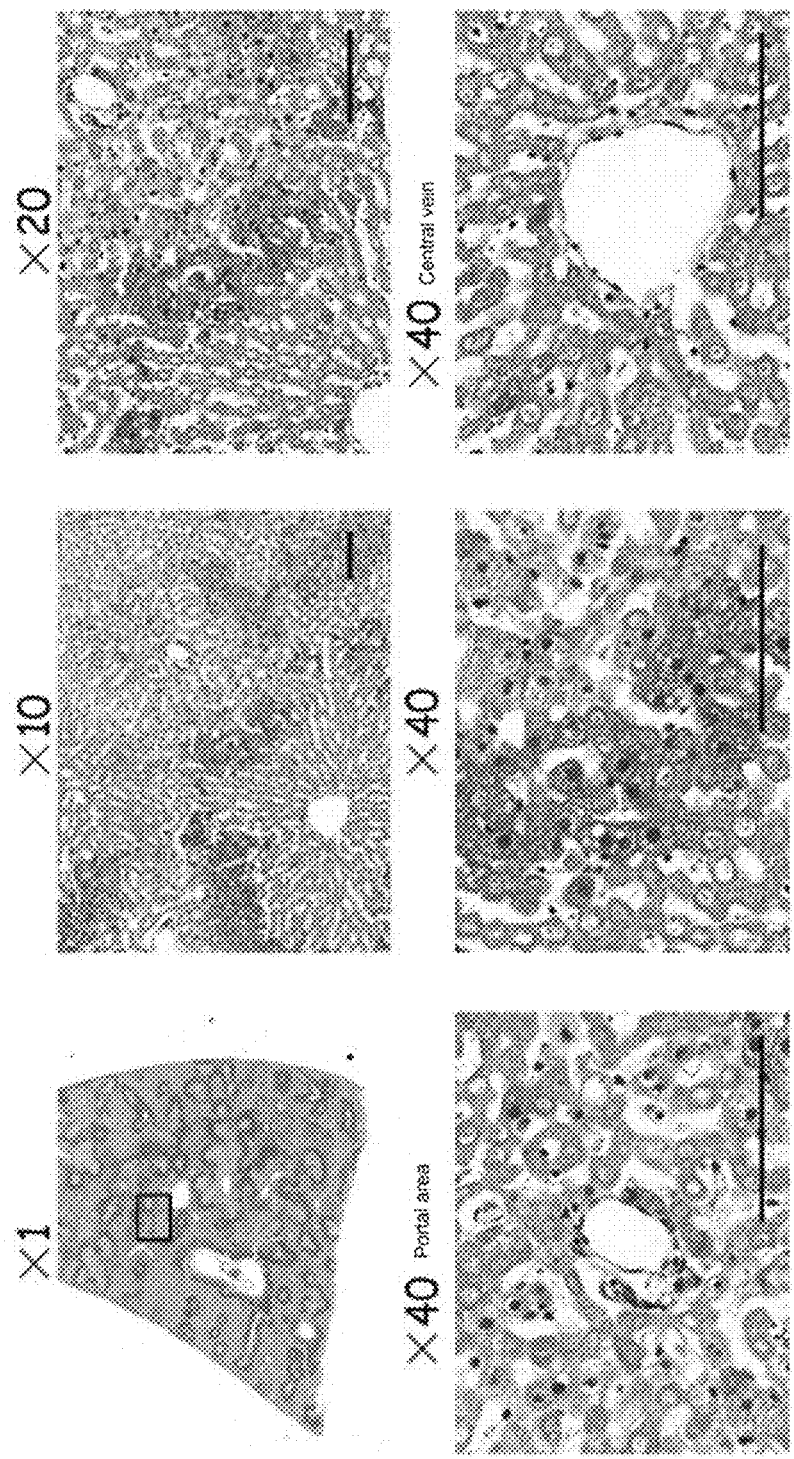

[Figure 11]
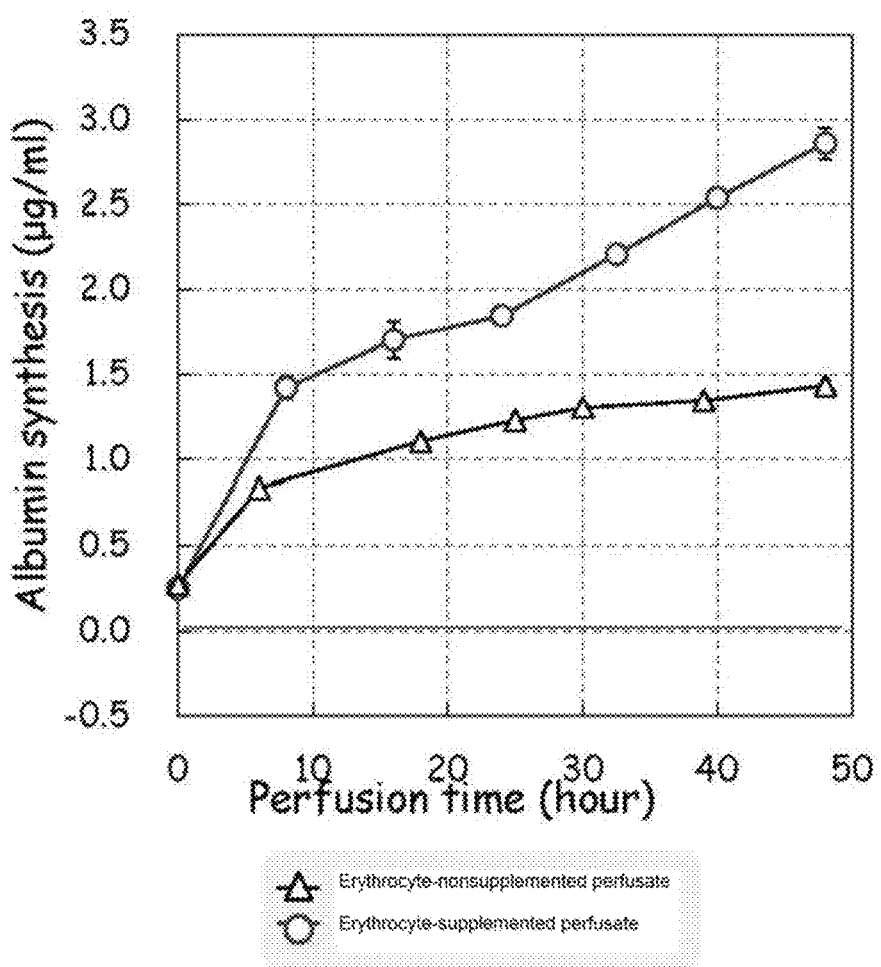

[Figure 12]
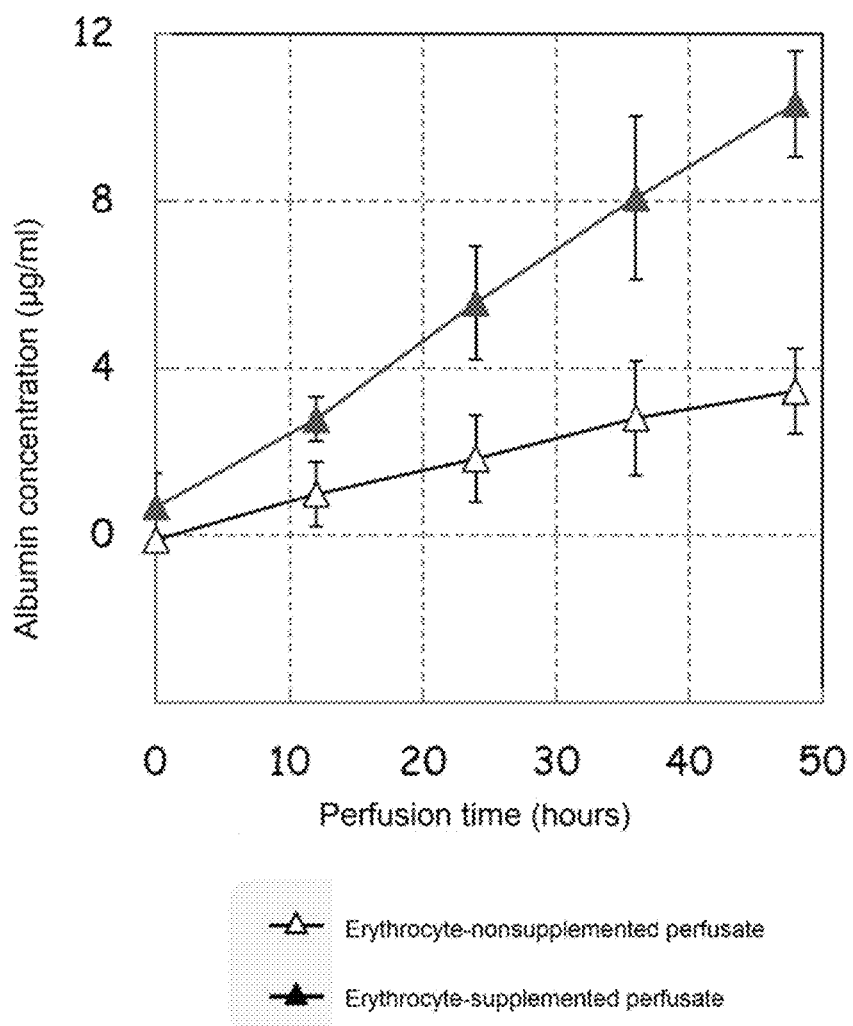

[Figure 13]
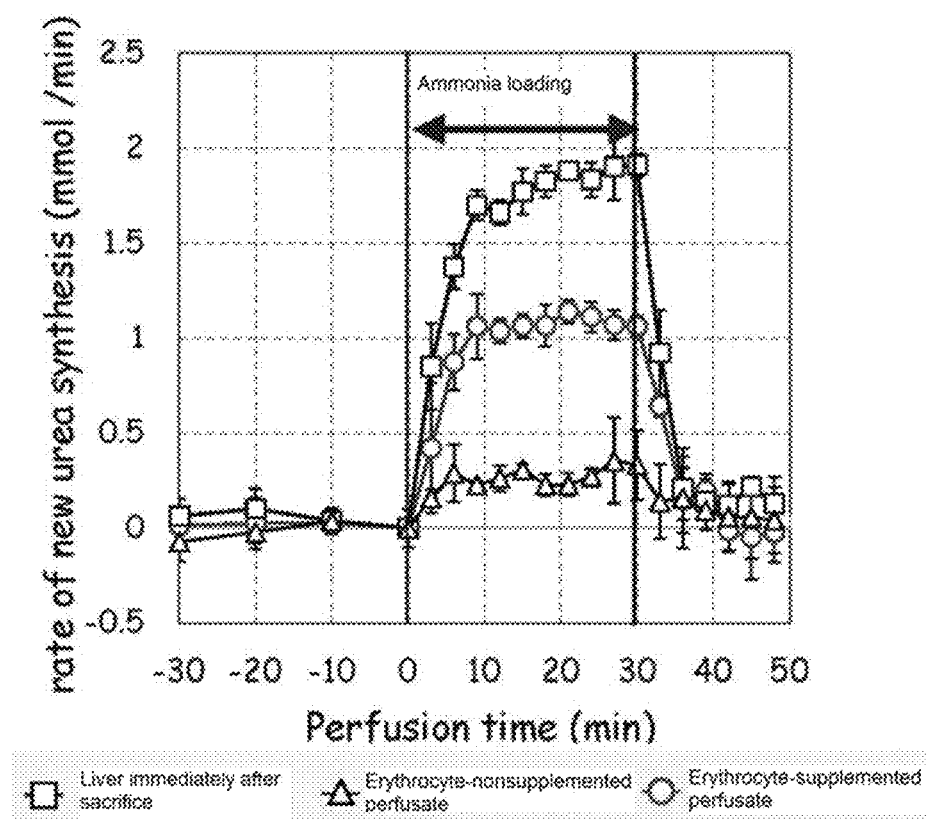

[Figure 14]
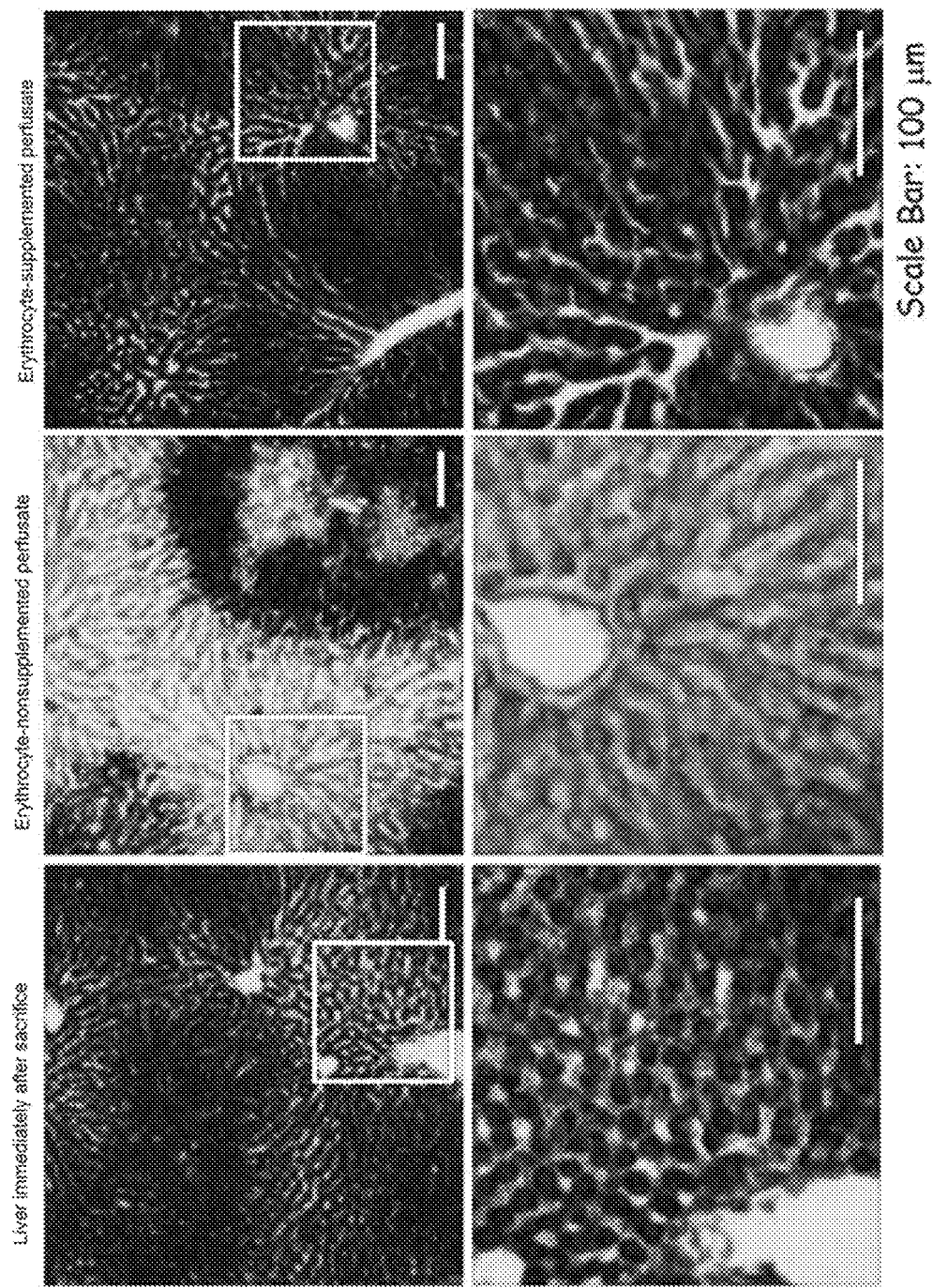

[Figure 15]
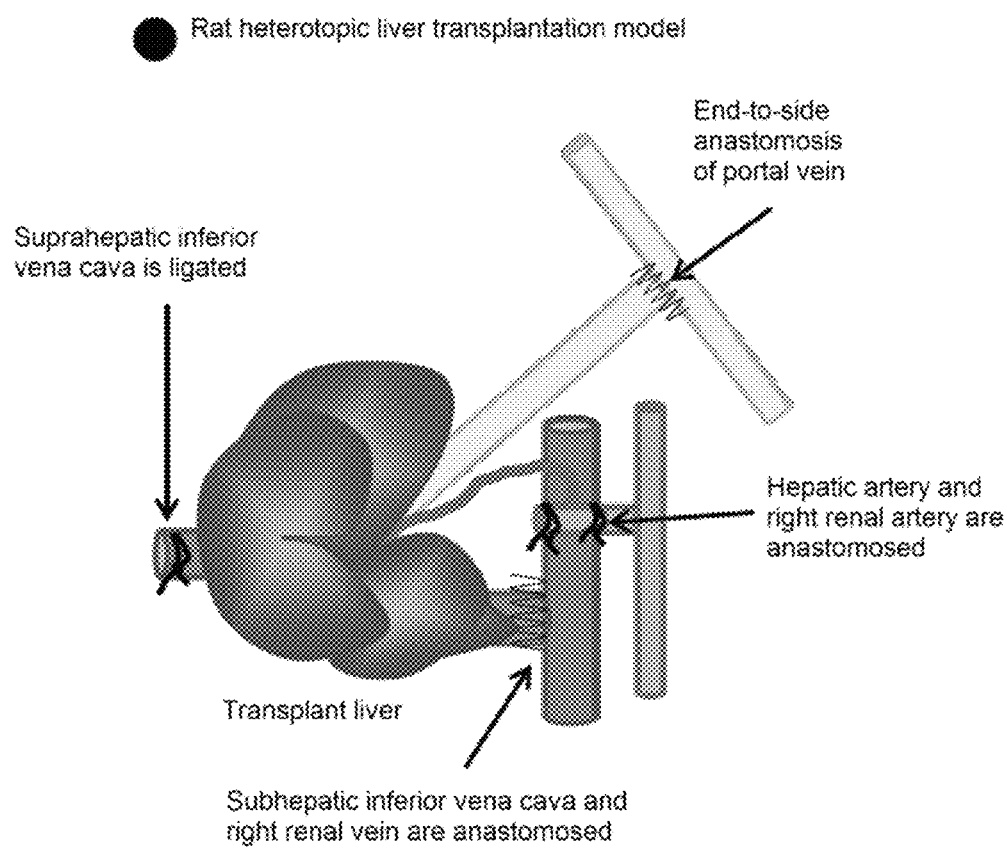

[Figure 16]
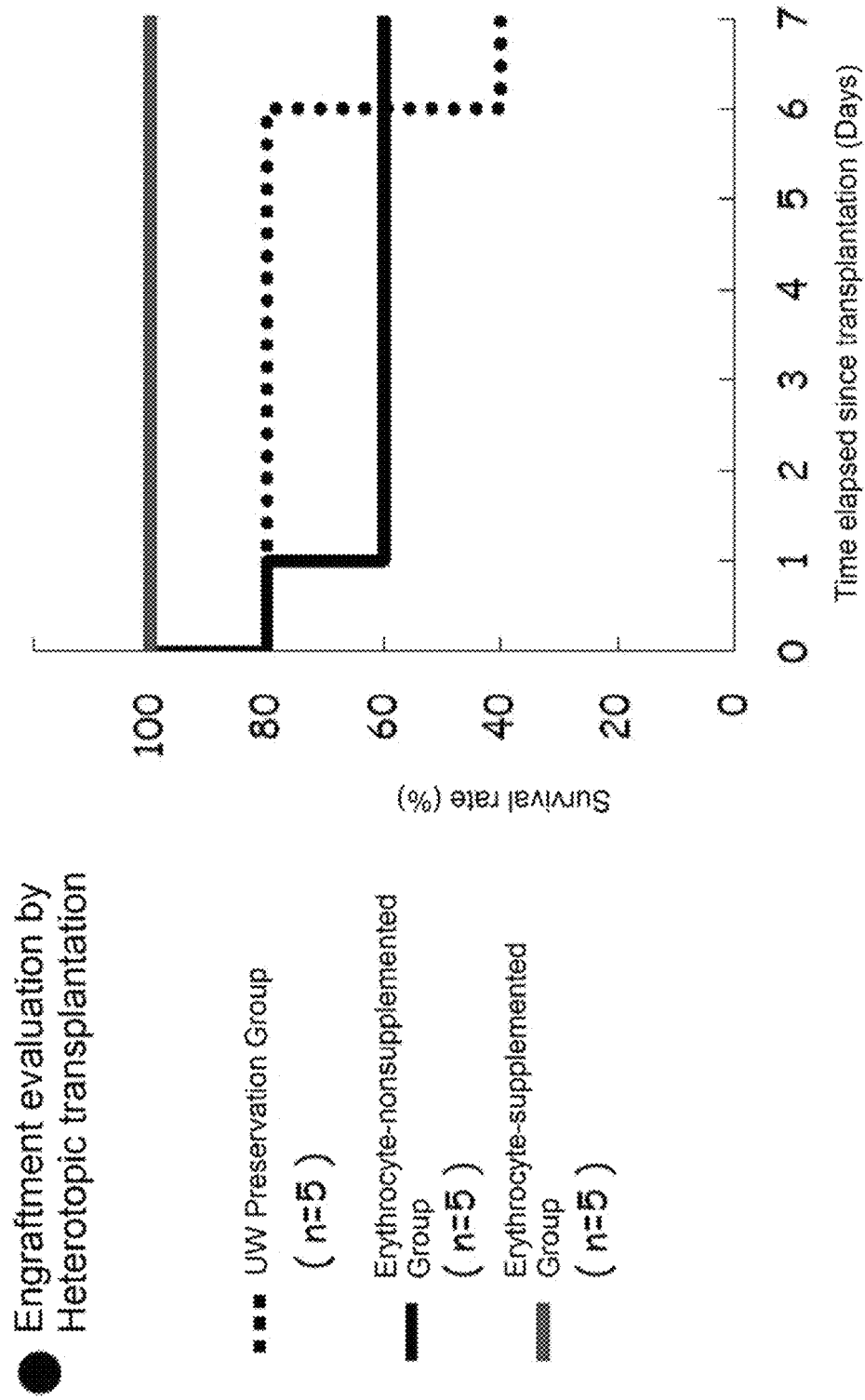

[Figure 17]
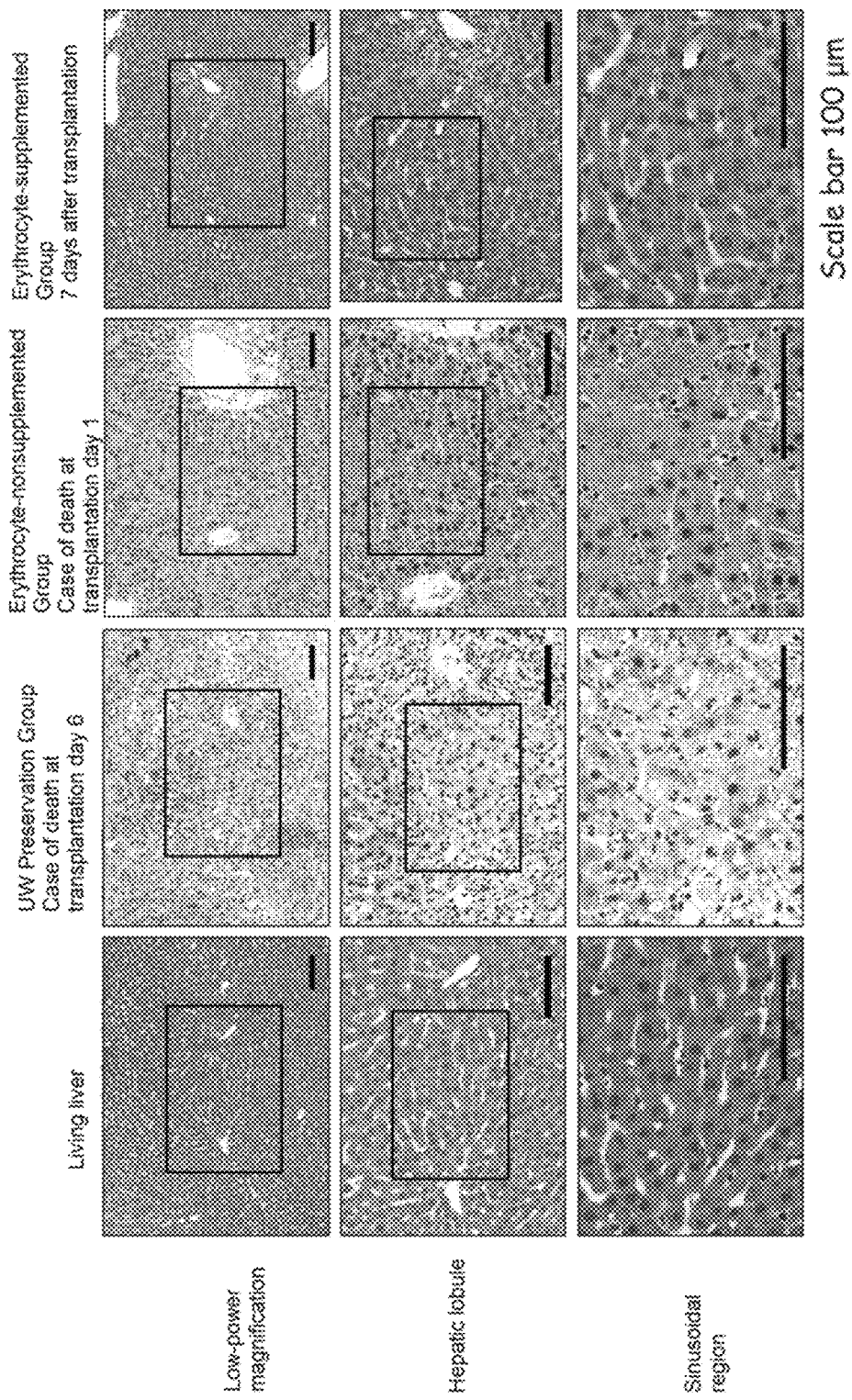

[Figure 18]
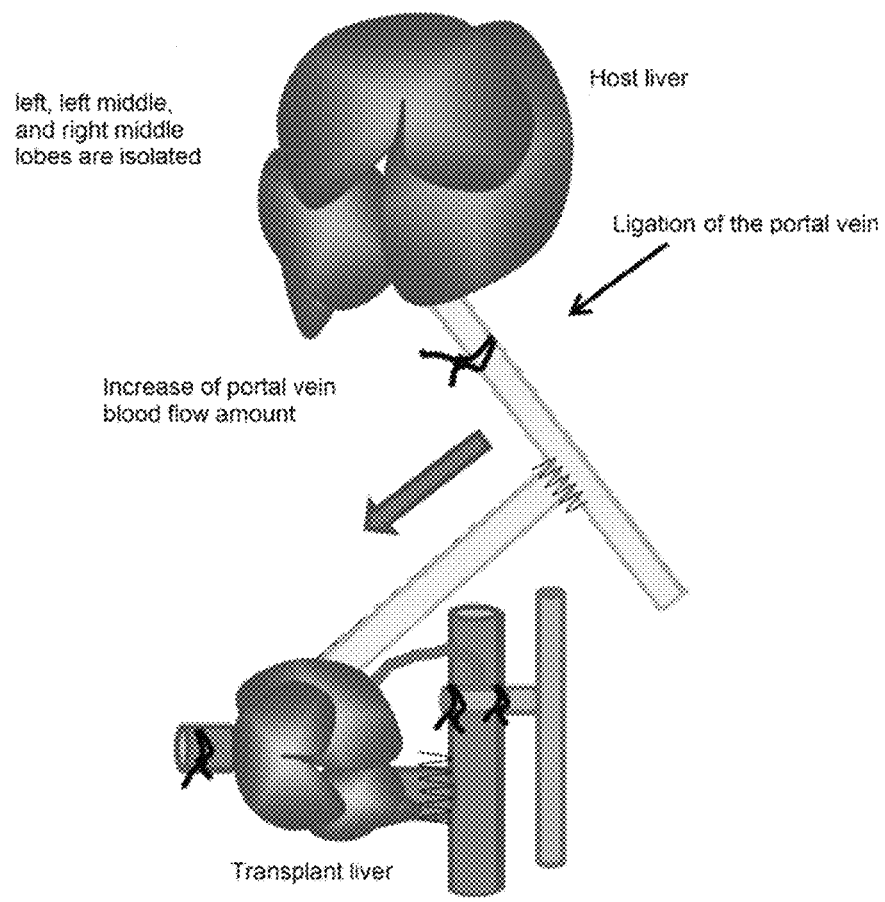

[Figure 19]
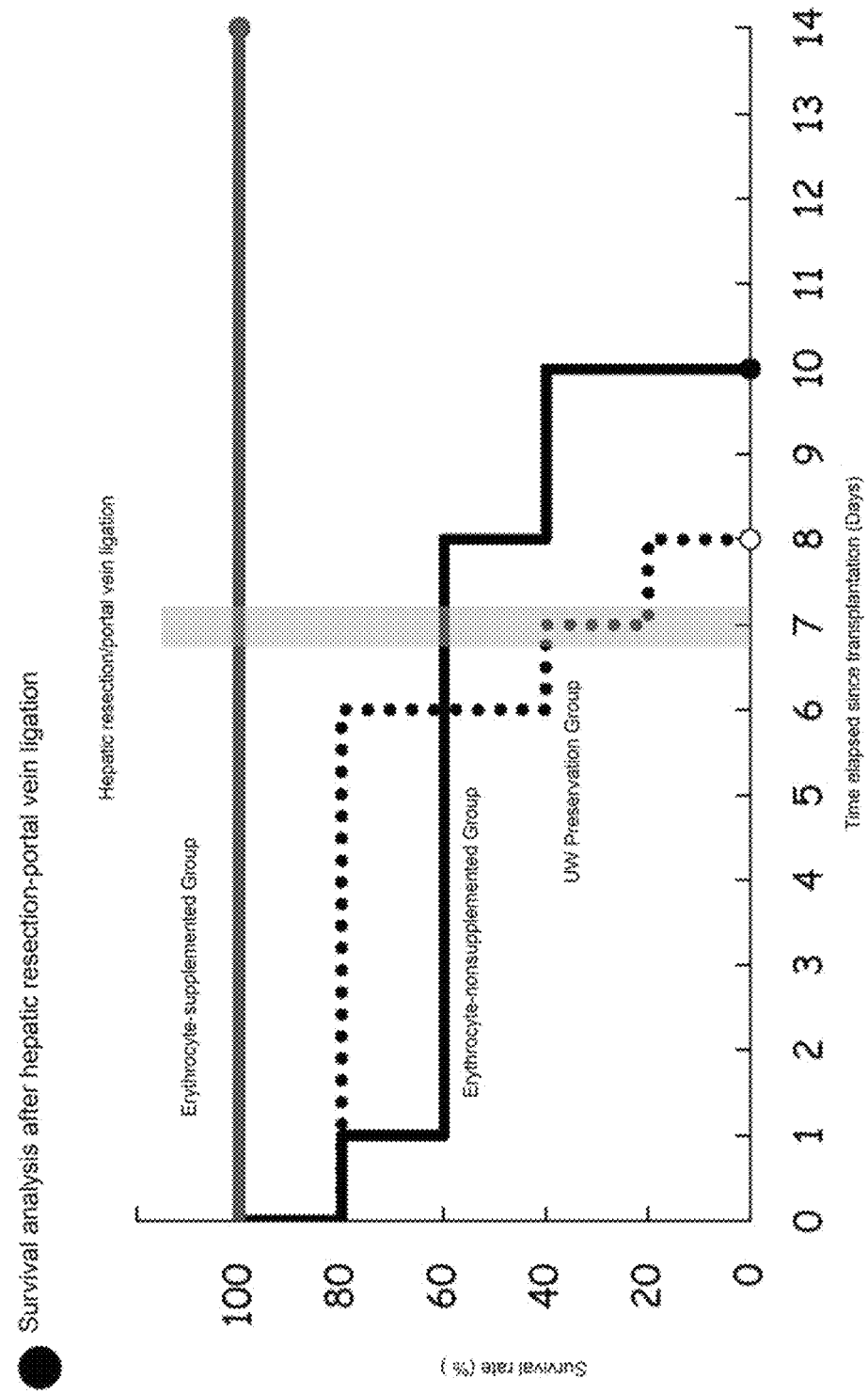

[Figure 20]
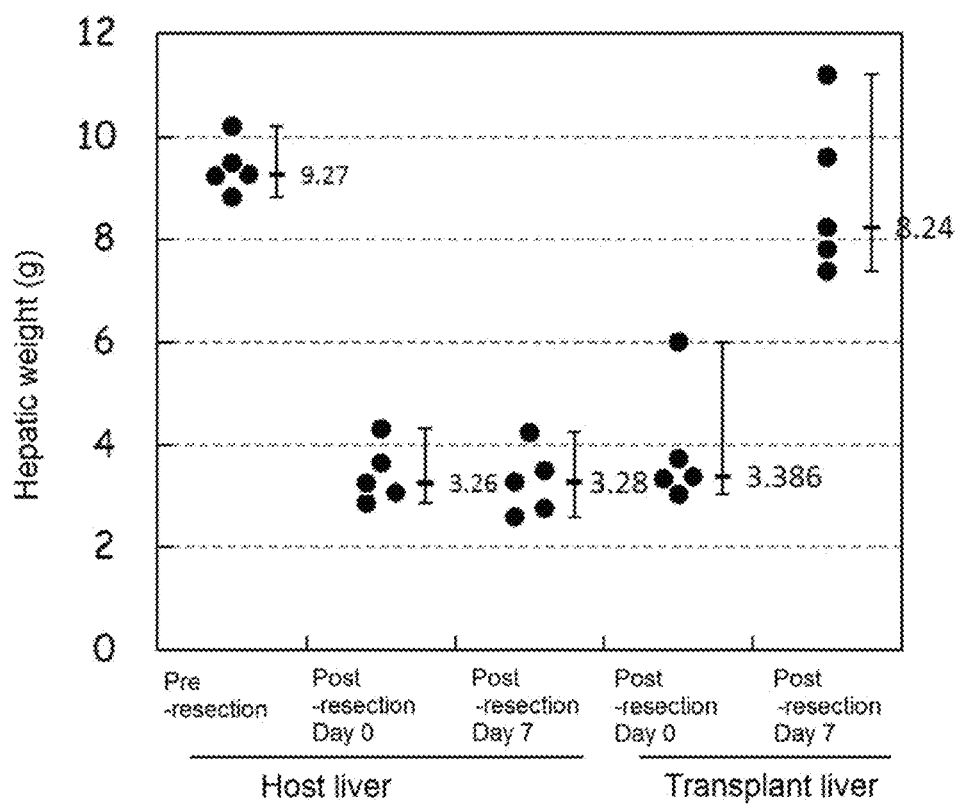

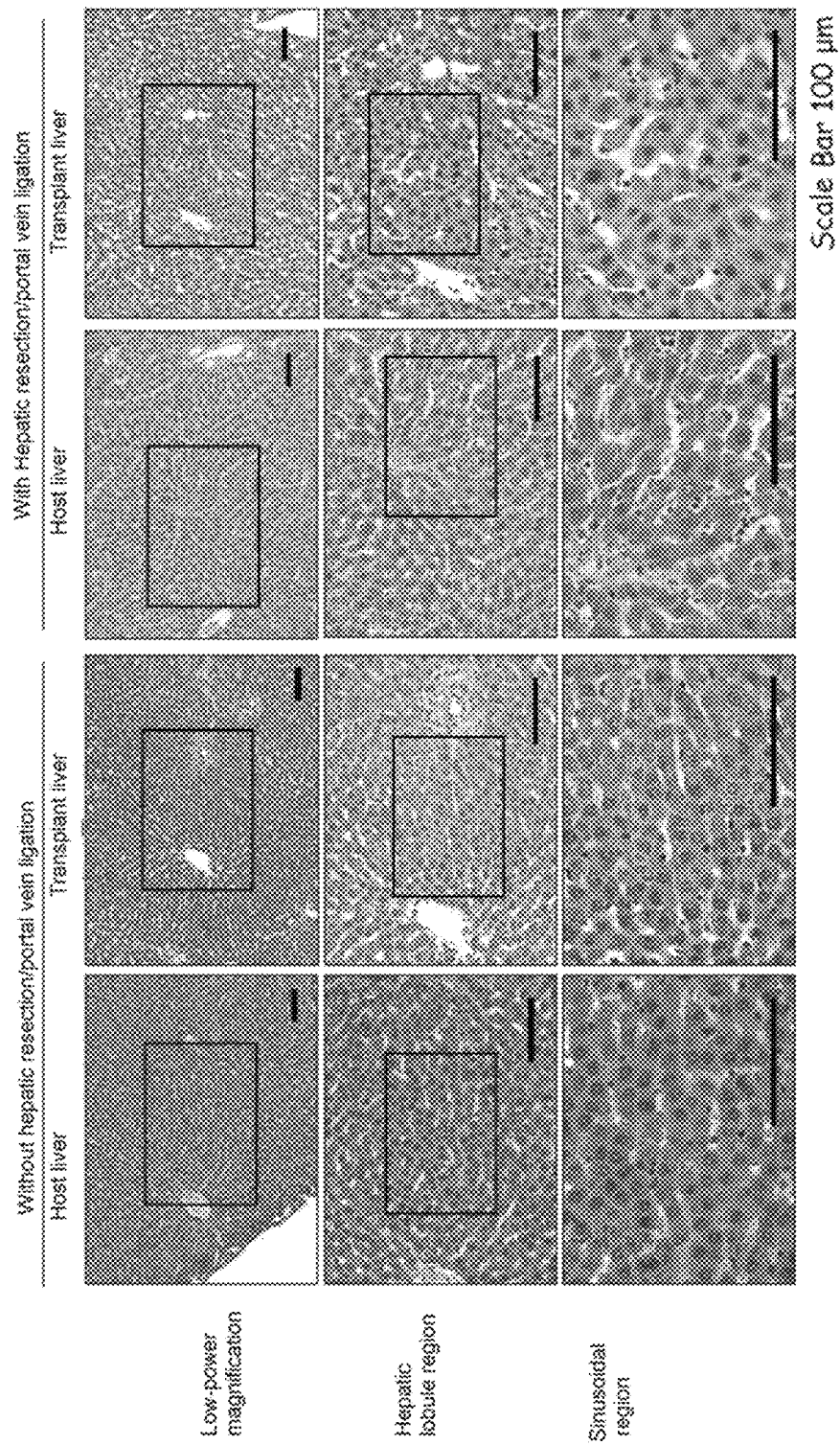
[Figure 21]

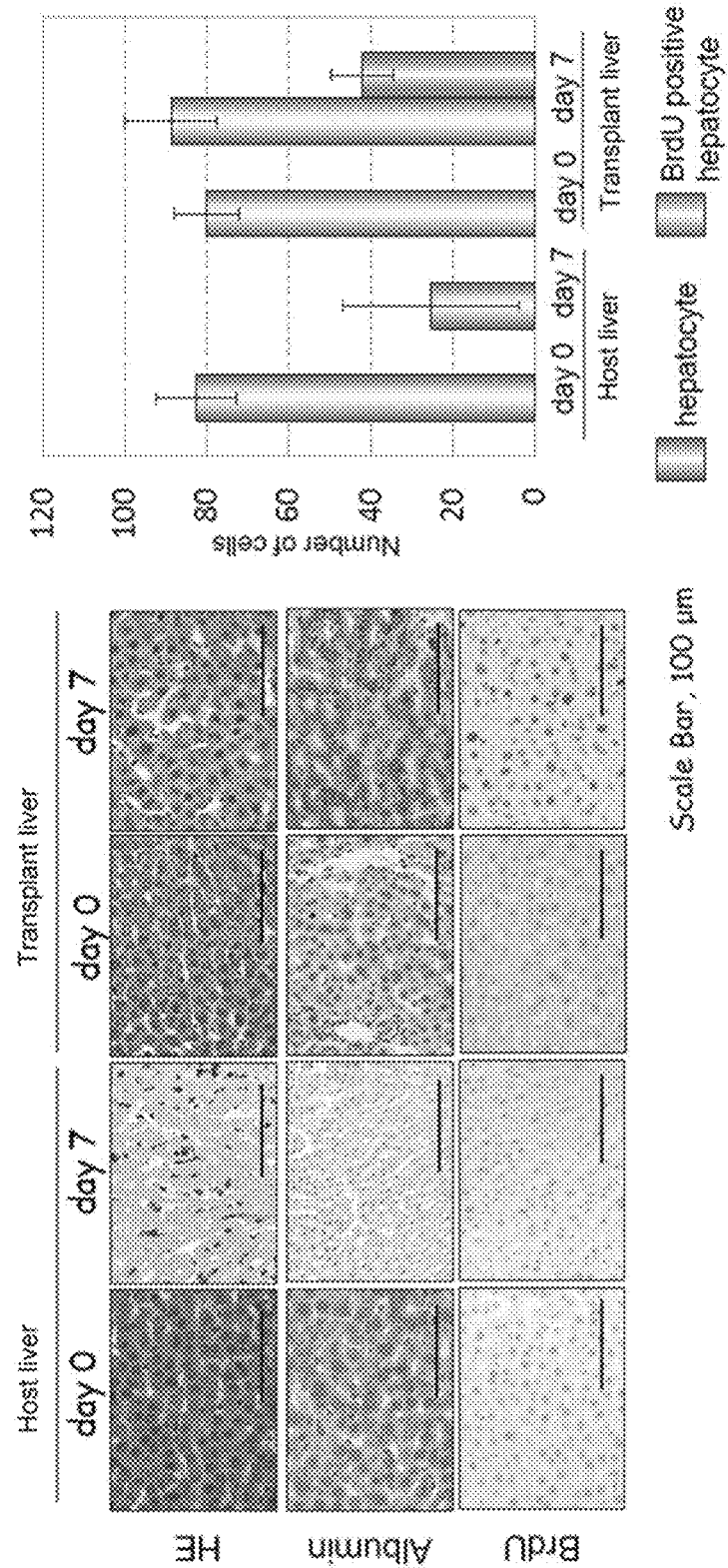
[Figure 22]

METHOD FOR MAINTAINING ORGAN OR TISSUE FOR TRANSPLANTATION USE FOR LONG PERIOD

This application is a U.S. National Stage Application under 35 U.S.C. §371 of International Application No. PCT/JP2013/073207, filed Aug. 29, 2013, which claims priority to Japan Application No. 2012-197986 filed Sep. 8, 2012. Each of the above-referenced applications is expressly incorporated by reference herein its entirety.

TECHNICAL FIELD

The present invention relates to a method for maintaining an organ or tissue mainly for transplantation for long-term preservation while maintaining the organ or tissue function, as well as a method for isolating an organ or tissue. The present invention also relates to an organ or tissue for transplantation.

BACKGROUND ART

Organ transplantation is currently performed as the main therapy for irreversible organ dysfunction due to illnesses or accidents. Although the number of transplantation cases have increased and the success rates thereof have dynamically risen by advances in immunosuppressing agents or transplantation technologies, chronic organ shortages are posing a serious problem in transplantation medical care (Non-Patent Literature 1). Even though a method for transplanting a transplant animal organ or a development of gene-modified animals with less tendency to cause immunological rejection (Non-Patent Literatures 2 and 3), and further a development of artificial organs aiming to replace organ functions with artificial materials have been promoted in order to accommodate for this organ shortage (Non-Patent Literature 4), none of the technology developments have reached a point of replacing adult organ function.

The shortage of donor organs provided for transplantation is not only because of the number of organs provided, but the short duration that the isolated organ can be preserved in a transplantable state is also one great reason. For this reason, development of a technology for preserving the isolated organ ex vivo for a long-term in a transplantable state has been promoted. The method currently most broadly employed is a simple cooling method of replacing the blood in the organ with a low-temperature organ preservation solution and then immersing in a low-temperature preservation solution to suppress cell metabolism. There is also a perfusion cooling preservation method that perfuses the vascular plexus in the organ with a low-temperature organ preservation solution while performing immersion preservation at a low temperate in order to remove waste products in the organ in preservation, which is recently under trial in Europe and the U.S. (Non-Patent Literature 5).

However, safe expiration time of organs preserved by these methods is thought to be 60 hours for kidneys and 20 hours for livers in general, and an elongation technology for further duration of preservation has been desired.

Moreover, in addition to the above problems, another factor causing the shortage in the number of donor organs is that organs that can be provided are limited because the majority of donor registrants die of cardiac arrest. In organ transplantation from cardiac arrest donors, in contrast to organ transplantation from brain-dead donors, a period during which the blood flow to organs is stopped, in other words a period of "warm ischemia" occurs between cardiac arrest and isolation and preservation of organs. Cell swelling disorder the to depletion of ATP or accumulation of waste products such as hypoxanthine are caused in an organ or tissue in warm ischemic state. The hypoxanthine accumulated in cells is rapidly metabolized by the oxygenated perfusate when blood flow to the organ or tissue is resumed. During this process, tissue disorder may be provoked by the large amount of reactive oxygen produced, and systemic acute shock may be evoked in the recipient receiving the organ transplantation by cytokines etc. secreted from cells.

Because an organ or tissue becomes maladaptive for organ transplantation when warm ischemic state is continued for a few minutes due to organ or tissue disorder accompanying warm ischemia and reperfusion, the transplantation adaptation rate of organs from donors who have died from unexpected cardiac arrests outside hospitals is currently only 10% or less, and further the transplantation engraftment rate therefrom remains at about 70%. (Non-Patent Literature 6)

In other words, the transplantation adaptation rate of organs from cardiac arrest donors remain at a very low level compared to the transplantation adaptation rate of organs from brain-dead donors, and development of a technology that enables organ donation from cardiac arrest donors is desired in order to expand the number of donor organs.

CITATION LIST

[Non-Patent Literature 1] Lechler R I. et al.: Nat Med 11(6): 605, 2005
[Non-Patent Literature 2] Eventov-Friedman S. et al.: Proc. Natl. Acad. Sci. USA 102(8): 2928, 2005
[Non-Patent Literature 3] Yang Y G. et al.: Nat Rev. Immunol. 7(7): 519, 2007
[Non-Patent Literature 4] Malchesky P S. et al.: Artif Organs. 30(9): 655, 2006
[Non-Patent Literature 5] Moers C. et al.: N. Engl. J. Med 360(1): 7, 2009
[Non-Patent Literature 6] Fondevila C, et al.: Am. J. Transplant 12: 162-170, 2012

SUMMARY OF THE INVENTION

Problems to be Solved by the Invention

The object of the present invention is to provide a technology that enables long-term preservation while maintaining the function of an organ or tissue for transplantation. A further object is utilizing this technology to provide a technology for suppressing tissue disorder accompanying wane ischemia and reperfusion as well as restoring an organ or tissue from a cardiac arrest donor to a level compatible for transplantation.

Means for Solving the Problems

As a result of repeated investigations by the present inventors to solve the above problems, it was found that organ or tissue disorder can be maintained in a significantly suppressed state for a long time by perfusing an organ or tissue for transplantation with a perfusate comprising an oxygen carrier and a blood coagulation inhibitor.

The present inventors have also found that organ or tissue disorder can be further significantly suppressed by keeping the temperature of the organ or tissue during perfusion within a given range.

The present inventors have further found that an organ or tissue that has once come to be in a warm ischemic state can be restored to a state close to the organ or tissue before cardiac arrest by perfusing the organ or tissue that has come to be in a warm ischemic state due to cardiac arrest with a perfusate comprising an oxygen carrier and a blood coagulation inhibitor, and thus achieved the completion of the present invention.

In other words, the present invention provides a long-term maintenance method of a mammalian organ or tissue for transplantation that employs perfusion by a perfusate, comprising each of the following steps of (a) connecting a perfusate instream cannula for streaming said perfusate into said "organ or tissue," (b) connecting a perfusate outstream cannula for streaming said perfusate out from said "organ or tissue," and (c) perfusing a perfusate comprising an oxygen carrier and a blood coagulation inhibitor into said organ or tissue.

Here, one embodiment of the long-term maintenance method of a mammalian organ or tissue for transplantation according to the present invention is characterized in that said oxygen carrier in said step (c) is erythrocyte.

One embodiment of the long-term maintenance method of a mammalian organ or tissue for transplantation according to the present invention is characterized in that the perfusate in said step (c) is circulated.

One embodiment of the long-term maintenance method of a mammalian organ or tissue for transplantation according to the present invention is characterized in that it comprises a further subsequent step of (d) before said step (c), perfusing said "organ or tissue" with a perfusate comprising an oxygen carrier and a blood coagulation inhibitor to wash said "organ or tissue," and then removing the perfusate employed for said washing.

One embodiment of the long-term maintenance method of a mammalian organ or tissue for transplantation according to the present invention is characterized in that in said step (c), said "organ or tissue" is isolated together with a second "organ or tissue" that is continuous in vivo to said "organ or tissue," and perfusion is performed with said "organ or tissue" in a suspended state by immobilizing said second "organ or tissue".

One embodiment of the long-term maintenance method of a mammalian organ or tissue for transplantation according to the present invention is characterized in that in said step (c), said "organ or tissue" is immersed in a liquid so that at least a part thereof receives buoyancy.

One embodiment of the long-term maintenance method of a mammalian organ or tissue for transplantation according to the present invention is characterized in that in said step (c), said "organ or tissue" is placed under a temperature state maintained at 4° C.-37° C.

One embodiment of the long-term maintenance method of a mammalian organ or tissue for transplantation according to the present invention is characterized in that said blood coagulation inhibitor is heparin.

One embodiment of the long-term maintenance method of a mammalian organ or tissue for transplantation according to the present invention is characterized in that said "organ or tissue" is an "organ or tissue" selected from the grow consisting of the liver, the kidney, the pancreas, the heart, the lung, the stomach, the testis, the ovary, and the eyeball.

Moreover, according to another embodiment of the present invention, a method for isolating said "organ or tissue" for a long-tem) maintenance of a mammalian organ or tissue for transplantation is provided, comprising the following steps of (f) isolating said "organ or tissue" from said mammal, and (g) administering a blood coagulation inhibitor to said mammal before said step (f), wherein said mammal is a non-human or a human (but limited to a human who is a brain-dead patient).

Further, according to another embodiment of the present invention, a mammalian organ or tissue for transplantation is provided, characterized in that said "organ or tissue" is isolated from a mammal, and the blood in said "organ or tissue" is substituted by a perfusate comprising an oxygen carrier and a blood coagulation inhibitor.

Effects of the Invention

According to the long-tem) maintenance method of an organ or tissue according to the present invention, by perfusing an organ or tissue for transplantation with a perfusate supplemented with an oxygen carrier and a blood coagulation inhibitor, a disorder of an organ etc. after organ isolation can be maintained in a significantly suppressed state for a long time. Moreover, organ or tissue disorder can be maintained in a further significantly suppressed state for a long time by keeping the temperature of the organ or tissue during perfusion within a given range. Further, by perfusing an organ or tissue after cardiac arrest with a perfusate supplemented with an oxygen carrier and a blood coagulation inhibitor, the structure and function of an organ or tissue that has become untransplantable due to suffering disorder from warm ischemia can be restored to a transplantable state. In this way, long-term preservation is allowed while maintaining the function of an organ or tissue for transplantation in order to subject it to transplantation in a good state.

BRIEF DESCRIPTION OF THE DRAWINGS

FIG. 1 shows the schematic diagram of the perfusion circuit which is one embodiment of the present invention.

FIG. 2 shows the graph that compares the increase in ALT activity in the perfusate when the liver of rats immediately after sacrifice was perfused for 48 hours by altering the erythrocyte concentration condition in the perfusate.

FIG. 3 shows the tissue staining images of the liver of rats immediately after sacrifice, as well as the tissue staining images after the liver of rats immediately after sacrifice was perfused for 48 hours by altering the erythrocyte concentration condition in the perfusate.

FIG. 4 shows the graph that compares the increase in ALT activity in the perfusate when the liver of rats immediately after sacrifice was perfused by altering the liver temperature condition dining perfusion.

FIG. 5 shows the tissue staining images of the liver of rats immediately after sacrifice, as well as the tissue staining images after the liver of rats immediately after sacrifice was perfused by altering the liver temperature condition during perfusion.

FIG. 6 shows the schematic diagram of liver washing which is one embodiment of the present invention.

FIG. 7 shows the graph that compares the increase in ALT activity in the perfusate when the liver of warn ischemia model rats which is one embodiment of the present invention was perfused for 48 hours with an erythrocyte-supplemented or -nonsupplemented perfusate.

FIG. 8 shows the graph that compares the ALT activity in the perfusate dining liver washing before initiation of perfusion by the perfusion circuit in FIG. 7.

FIG. 9 shows the tissue staining images of the liver of warm ischemia model rats which is one embodiment of the present invention after 48 hours of perfusion with an erythrocyte-supplemented perfusate.

FIG. 10 shows the tissue staining images of the liver of warm ischemia model rats which is one embodiment of the present invention after 48 hours of perfusion with an erythrocyte-nonsupplemented perfusate.

FIG. 11 shows the comparison of the amount of albumin in the perfusate when the liver of warm ischemia model rats which is one embodiment of the present invention was perfused for 48 hours with an erythrocyte-supplemented or -nonsupplemented perfusate.

FIG. 12 shows the comparison of the amount of albumin in the perfusate when the liver of warm ischemia model rats which is one embodiment of the present invention was perfused for 48 hours with an erythrocyte-supplemented or -nonsupplemented perfusate.

FIG. 13 show the graph of the results of measurement of urea synthesis ability when ammonia loading test was performed with the liver of warm ischemia model rats perfused for 48 hours with an erythrocyte-supplemented or -nonsupplemented perfusate which is one embodiment of the present invention and the liver of rats immediately after sacrifice.

FIG. 14 shows the tissue images of when the intrahepatic vascular plexus of warm ischemia model rats perfused for 48 hours with an erythrocyte-supplemented or -nonsupplemented perfusate which is one embodiment of the present invention and rats immediately after sacrifice were solidified with gelatin comprising a fluorescent dye.

FIG. 15 shows the schematic diagram of when heterotopic transplantation is performed on a recipient rat with the liver of a warm ischemia model rats.

FIG. 16 is the graph showing the survival rate of recipient rats when heterotopic transplantation was performed after perfusion or preservation of the liver of warm ischemia model rats by various methods.

FIG. 17 shows the tissue images of the liver after transplantation when heterotopic transplantation was performed after perfusion or preservation of the liver of warm ischemia model rats by various methods.

FIG. 18 shows the schematic diagram of when the liver of a warm ischemia model rat is heterotopically transplanted to a recipient rat, and then the host liver is partially resected and the portal vein leading to the host liver is ligated.

FIG. 19 is the graph showing the survival rate of recipient rats when the liver of warm ischemia model rats is heterotopically transplanted, and then the host liver is partially resected and the portal vein leading to the host liver is ligated.

FIG. 20 is the graph of measuring the change in the host and transplant liver weights when the liver of warm ischemia model rats is heterotopically transplanted, and then the host liver is partially resected and the portal vein leading to the host liver is ligated.

FIG. 21 shows the tissue images of the host and transplant livers after 1 week after the host liver is partially resected and the portal vein leading to the host liver is ligated.

FIG. 22 shows the immunostaining images (albumin, BrdU) of the host and transplant livers after 1 week after the host liver is partially resected and the portal vein leading to the host liver is ligated, as well as the graph representing the number of hepatocytes or the number of BrdU positive hepatocytes within a certain field range.

DESCRIPTION OF EMBODIMENTS

<Long-Term Maintenance Method of Organ or Tissue>

The first embodiment of the present invention is a long-term maintenance method of a mammalian organ or tissue for transplantation that employs perfusion by a perfusate, characterized in that it comprises each of the following steps of (a) connecting a perfusate instream cannula for streaming said perfusate into said "organ or tissue," (b) connecting a perfusate outstream cannula for streaming said perfusate out from said "organ or tissue," and (c) perfusing a perfusate comprising erythrocytes and a blood coagulation inhibitor into said organ or tissue.

The "long-term maintenance" of an organ or tissue herein refers to a long-term maintenance while maintaining the function of an organ or tissue for transplantation, i.e. while maintaining a transplantable state, and the method therefor is not particularly limited. For example, by perfusing an organ or tissue for transplantation with a perfusate comprising erythrocytes and a blood coagulation inhibitor, organ or tissue disorder after organ isolation can be maintained in a significantly suppressed state for a long time.

Note that the maintenance method of a mammalian organ or tissue for transplantation that employs perfusion by a perfusate herein is a method that restores organ or tissue function by maintaining organ or tissue metabolism, and can be apprehended as organ or tissue culture that employs the perfusate as the culture medium.

The "transplantation" of an organ or tissue herein refers to moving and implanting an organ or tissue from the organ or tissue donor to the recipient, and the type of transplantation is not particularly limited. The type of transplantation includes, e.g. in terms of classification by the relationship between the donor and the recipient, autologous transplantation, isogeneic transplantation, allogeneic transplantation, heterologous transplantation, and the like, and e.g. in terms of classification by the state of the donor, living transplantation, brain-death death transplantation, cardiac arrest transplantation, and the like.

An "organ or tissue" herein is not particularly limited as long as it is an organ or tissue that can be employed for perfusion, examples of which include the heart, the liver, the kidney, the lung, the pancreas, the stomach, the small intestine, the large intestine, the testis, the ovary, the eyeball, the tooth and surrounding tissues thereof the hair and surrounding tissues thereof and the like.

An "organ or tissue" herein when the donor is a non-human may be an organ or tissue wherein perfusate instream and outstream cannulae are connected to an organ or tissue for transplantation and the organ or tissue is isolated after initiating perfusion. When the donor is a human, it may be an organ or tissue wherein perfusate instream and outstream cannulae are connected and perfusion is initiated after isolating the organ or tissue for transplantation.

For a "perfusate" herein, a well-known composition or a composition pursuant thereto can be appropriately selected by those skilled in the art according to the subject type of mammal or type of organ or tissue. Examples may be those comprising nutrients such as sugars or amino acids necessary for cell survival. A culture medium employed for general cell culture or a preservation solution employed for organ preservation and the like can be employed, the compositions of which are not particularly limited. The perfusate may also comprise e.g. sugars (glucose, trehalose, raffinose), thickeners (HES, dextran), antioxidants (N-acetylcysteine, allopurinol, glutathione), vasodilators (nitroglycerin), and cytokines/growth factors (IGF, FGF, EGF, HGF).

The "perfusion" of an organ or tissue herein refers to linking tubes such as perfusate instream and outstream cannulae to the blood vessels of an organ or tissue for transplantation, and streaming the perfusate into and out of the organ or tissue similarly to blood flow. For example, when the organ to be perfused is the liver, the perfusate can be streamed in from the portal vein and streamed out from the suprahepatic inferior vena cava, but a route to stream in the perfusate from the hepatic artery can also be employed. Even when an organ other than the liver is employed, those skilled in the art can select appropriate blood vessels to be employed for perfusate instream and outstream and employ them for perfusion.

A "mammal" herein is not particularly limited, and the maintenance method according to the present invention can be utilized for any and all mammalian organ or tissue. When an organ or tissue maintained with the method according to the present invention is employed for transplantation, the mammal can be appropriately selected according to the subject (recipient) for transplanting the organ or tissue, examples of which can include a human, a pig, a cow, a monkey, a baboon, a dog, a cat, a rat, a mouse, and the like. When the donor is a human, the organ or tissue mainly employed can be an organ or tissue of a brain-dead donor, but it is not limited thereto and an organ or tissue of a cardiac arrest donor may also be employed. Further, the long-term maintenance method according to the present invention can also be employed for example when an organ or tissue for transplantation into a human that was cultured in vivo in a non-human mammal such as by genetic recombination technology is employed.

A "cannula" herein is not particularly limited as long as it is a tube etc. for inserting into the blood vessel, and can be appropriately selected according to the type or size of the organ or tissue, the composition of the perfusate, and the like.

In the first embodiment of the present invention, it is preferred that a blood coagulation inhibitor is administered before cardiac arrest of the mammal to be the donor. By administering a blood coagulation inhibitor before cardiac arrest of the mammal, blood coagulation in the blood vessels of the organ or tissue after cardiac arrest is suppressed, and circulatory failure that may occur in the organ or tissue after initiation of perfusion can be prevented. However, circulatory failure preventive effect by the blood coagulation inhibitor comprised in the perfusate can be sufficiently obtained even without administration of a blood coagulation inhibitor before cardiac arrest.

A "blood coagulation inhibitor" herein is not particularly limited as long as it is a substance that has the effect of acting on the blood coagulation system to inhibit coagulation, examples of which include heparin, warfarin, acenocoumarol, phenindione, and the like. When a blood coagulation inhibitor is administered before cardiac arrest, the administration method is not particularly limited. For example, when the blood coagulation inhibitor is heparin, it can be intravenously administered, and when the blood coagulation inhibitor is warfarin, acenocoumarol, phenindione, and the like, it can be orally administered. Intravenous and oral administrations of the blood coagulation inhibitor can also be used in combination. For example, when heparin is intravenously administered before cardiac arrest, it is preferably administered in the range of 20-4000 units, and further preferably administered in the range of 40-2500 units.

Moreover, the amount of the blood coagulation inhibitor comprised in the perfusate employed for organ or tissue perfusion can be appropriately selected by those skilled in the art according to the type of mammal or organ. For example, when the blood coagulation agent comprised in the perfusate is heparin, the amount of heparin comprised in the perfusate is preferably in the range of 2500-80000 units per 1 L of perfusate, and further preferably in the range of 40000-60000 units per 1 L of perfusate.

The method for supplementing an oxygen carrier to the perfusate herein is not particularly limited, and it may be supplemented after preparing the perfusate or supplemented simultaneously with the preparation of the perfusate. Moreover, in one embodiment, by keeping the dissolved oxygen concentration in the perfusate constant, perfusion can be performed while maintaining the function of the supplemented oxygen carrier for a long time. The method for keeping the dissolved oxygen in the perfusate constant is not particularly limited, and e.g. a simplified animal cell culture device (ABT F, Tokyo, Japan) can be employed to maintain the dissolved oxygen concentration in the perfusate at 6.5-7.5 mg/L.

An "oxygen carrier" herein is not particularly limited as long as it has the function to carry oxygen by binding thereto. For example, erythrocyte, perfluorocarbon, hemoglobin endoplasmic reticulum, artificial erythrocyte, and the like can be employed.

Note that when "erythrocyte" is employed as the "oxygen carrier" herein, the "erythrocyte" is not particularly limited as long as it can be supplemented to the perfusate, and erythrocytes from various mammals can be employed. Examples of animals for collecting erythrocytes can include humans, pigs, cows, monkeys, baboons, dogs, cats, rats, mice, and the like. When the recipient for transplanting an organ or tissue is a human, the erythrocytes employed are preferably those collected from the recipient itself in terms of suppressing rejection from transplantation. Moreover, even when erythrocytes collected from the recipient itself are not employed, it is preferred to employ erythrocytes of the same blood type as the recipient in terms of suppressing rejection from transplantation. The method for preparing erythrocytes is also not particularly limited, and for example it can be prepared by diluting blood collected from a mammal with a culture medium, subjecting to centrifugation, and then washing the blood plasma component.

The concentration of the oxygen carrier in the perfusate herein can be appropriately set by those skilled in the art according to the subject organ or tissue and the type of oxygen carrier used. For example, when "erythrocytes" are employed as the oxygen carrier, the erythrocyte concentration in the perfusate is preferably $0.5 \times 10^{11}$ cells-$50.0 \times 10^{11}$ cells per 1 L of perfusate, further preferably $1.0 \times 10^{11}$ cells-$50.0 \times 10^{11}$ cells per 1 L of perfusate, and most preferably $2.0 \times 10^{11}$ cells-$50.0 \times 10^{11}$ cells per 1 L of perfusate. When the erythrocyte concentration in the perfusate is less than $0.5 \times 10^{11}$ cells per 1 L of perfusate, oxygen supply to the organ will be insufficient and necrosis of cells in the organ will occur, and when it is greater than $50.0 \times 10^{11}$ cells per 1 L of perfusate, organ disorder due to erythrocyte infarction during perfusion may occur.

The perfusion of an organ or tissue herein can be performed while maintaining the temperature of the organ or tissue in a state of 4° C.-37° C., preferably performed while the temperature of the organ or tissue in a state of 15° C.-33° C., and most preferably performed while maintaining a state of 20° C.-25° C. During organ or tissue perfusion, organ dysfunction the to low temperature injury is caused when the temperature of the organ or tissue is lower than 4° C., and increase in liver disorder value is seen when it is greater than 37° C.

The method for maintaining an organ or tissue in perfusion at a constant temperature herein is not particularly limited. For example, the organ or tissue can be maintained at a constant temperature by performing perfusion while maintaining the temperature of the liquid in which the organ or tissue is floated at a desired temperature. Preferably, the temperature of the organ or tissue can be maintained at a desired temperature by maintaining the temperature of the perfusate perfused to the organ or tissue at room temperature (25° C.)-37° C., and maintaining the temperature of the liquid in which the organ or tissue is floated at 20° C.-25°.

The device for maintaining an organ or tissue in perfusion at a constant temperature is not particularly limited. For example, a heater etc. may be employed to externally apply temperature change to a vessel comprising the organ or tissue, or a device for managing the temperature of the perfusate itself etc. may be employed to directly apply temperature change to the perfusate.

"Circulating the perfusate" herein means that the perfusate streamed out from the perfusate outstream cannula connected to the organ or tissue is not discarded but is streamed into the organ or tissue again through the perfusate instream cannula, and this is repeated.

Perfusing the perfusate to an organ or tissue to "wash" the organ or tissue herein means that the perfusate is streamed into/out of the blood vessels of the organ or tissue, and the perfusate streamed out is removed without circulation. By washing the organ or tissue with the perfusate, reactive oxygen, cell autolysate, microthrombus, and the like which have accumulated in the organ or tissue in which blood flow have stopped due to cardiac arrest are removed, and this can reduce organ or tissue disorders caused therefrom.

In the maintenance method according to the present invention, an organ or tissue that was isolated together with a second organ or tissue that is continuous in vivo to the organ or tissue can be employed. According to such configuration, because said second organ or tissue can be immobilized to suspend the organ or tissue to be perfused when performing perfusion, the perfusate can be delivered to every part of the organ or tissue without damaging the organ or tissue to be perfused.

The second organ or tissue is preferably an organ or tissue that is continuous in vivo to the organ or tissue, and more preferably an organ or tissue that is continuous in vivo to the upper portion of the organ or tissue. The organ or tissue can be perfused in an environment similar to the in vivo configuration by suspending with such an organ or tissue. An environment similar to the in vivo configuration here means an environment in which the organ or tissue can maintain its natural form without being compressed from hard materials such as the inner surface of the vessel. Since conventional organ or tissue perfusion was performed by placing the organ or tissue on a vessel such as a dish, blood vessels in the portion contacting the dish were compressed and the perfusate was not sufficiently delivered. According to the above embodiment, because the organ or tissue is suspended and perfused in an environment similar to the in vivo configuration, the perfusate can be delivered to the entire organ or tissue.

Moreover, when immobilizing the second organ or tissue, since it is permissible for the second organ or tissue to be damaged, immobilization can be done firmly with a method such as inserting a support tube, pinching with a clip, or stitching with a surgical suture. For example, when the organ to be perfused is the liver, the diaphragm is continuous upperside thereto in vivo and said diaphragm is connected to the costal bone, and thus only the diaphragm or both the diaphragm and the costal bone can be employed as the second organ or tissue. If the diaphragm is isolated together when isolating the liver from a mammal, the liver can be suspended in an environment close to that in vivo by immobilizing said diaphragm. If the costal bone in addition to the diaphragm is isolated together, a more stable suspension will be possible because the costal bone can be immobilized.

Other examples of the second organ or tissue include, but are not limited to, the fat tissue attached to the surface of these organs when perfusing the kidney or the pancreas; the upstream adjacent organs when perfusing the gastrointestinal system organs (specifically, the stomach or the duodenum when perfusing the small intestine or the small intestine when culturing the large intestine); the jaw bone, the alveolar bone, the tooth root bone, and the gingiva when perfusing the tooth and surrounding tissues thereof the epidermis, dermis, and fat tissue when perfusing the hair and surrounding tissues thereof and the like.

It is preferred that the maintenance method according to the present invention is performed with the organ or tissue immersed in a liquid so that at least a part thereof receives buoyancy in the perfusion step. By doing so, at least a part of the organ or tissue will receive buoyancy, thus enabling creation of an environment further closer to the in vivo configuration compared to simple suspension, and the perfusate can be delivered to every part of the organ or tissue. The organ or tissue is preferably in a state that at least 30% thereof exists in the liquid, more preferably 50%, further preferably 80%, and most preferably in a state that the entirety exists in the liquid.

The liquid for immersing the organ or tissue, similarly to the perfusate, can be appropriately selected by those skilled in the art according to the type of mammal and organ etc., and may have the same or different composition as the perfusate.

In the maintenance method according to the present invention, it is preferred that perfusion is performed with the organ or tissue in an immobilized state in a perfusion vessel for organ immobilization. For the organ or tissue to be immobilized to the perfusion vessel for organ immobilization, an organ or tissue that was isolated together with a second organ or tissue that is continuous in vivo to the organ or tissue for transplantation can be employed. The perfusion vessel for organ immobilization is provided with a suspensory means with which the organ for transplantation is suspendable with said second organ or tissue. The inside of the perfusion vessel for organ immobilization can be filled with a liquid, and is configured so that the organ or tissue can be immersed to give buoyancy to at least a part thereof. The perfusion vessel for organ immobilization may be of any material, and can be fabricated with e.g. glass or acrylic. In the perfusion vessel for organ immobilization, an organ or tissue for transplantation is immobilized by suspension by said second organ or tissue, and the organ or tissue for transplantation is in a state immersed in a liquid during perfusion, thereby allowing the perfusate to be delivered to every part of the organ or tissue without damaging the organ or tissue to be perfused.

In other words, the present invention in one embodiment can be referred to as a maintenance device for an organ or tissue comprising a perfusate comprising an oxygen carrier and a blood coagulation inhibitor, a perfusate instream cannula for streaming the perfusate into said organ or tissue, and a perfusate outstream cannula for streaming the perfusate out of said organ or tissue.

Moreover, said maintenance device in one embodiment may comprise a suspensory means for suspending said organ or tissue. Further, said maintenance device may further comprise a vessel that enables immersion of at least a part of said organ or tissue in the organ or tissue immersion liquid with said organ or tissue in a suspended state.

The method for measuring the degree of damage of an organ or tissue herein is not particularly limited, and can be appropriately selected by those skilled in the art according to the subject organ or tissue. For example, when the subject organ or tissue is the liver, the degree of hepatic damage can be measured by liver disorder enzyme (ALT) activity, histological analysis, measurement of bile production amount, measurement of albumin synthesis amount, measurement of urea synthesis by ammonia loading test, analysis of the intrahepatic capillary plexus, and the like.

<Method for Resecting Organ or Tissue>

The second embodiment of the present invention is a method for isolating an organ or tissue for maintaining a mammalian organ or tissue for a long time for transplantation, characterized in that it comprises the following steps of (f) isolating said "organ or tissue" from said mammal, and (g) administering a blood coagulation inhibitor to said mammal before said step (f), wherein said mammal is a non-human or a human (but limited to a human who is a brain-dead patient). The terms used in the first embodiment of the present invention will be employed synonymously in the second embodiment, and descriptions therefor will be omitted.

In the second embodiment of the present invention, by administering a blood coagulation inhibitor before cardiac arrest of the donor, blood coagulation in the blood vessels of the organ or tissue after cardiac arrest is suppressed, and circulatory failure that may occur in the organ or tissue after initiation of perfusion can be prevented.

In the second embodiment of the present invention, the administration method of the blood coagulation inhibitor is not particularly limited. For example, when the blood coagulation inhibitor is heparin, it can be intravenously administered, and when the blood coagulation inhibitor is warfarin, acenocoumarol, phenindione, and the like, it can be orally administered. Intravenous and oral administrations of the blood coagulation inhibitor can also be used in combination. The dosage of the blood coagulation inhibitor is also not particularly limited, and can be appropriately prepared by those skilled in the art according to the type, the age in weeks, and the weight etc. of the mammal to be administered the blood coagulation inhibitor.

The timing for isolating an organ or tissue for transplantation from the donor herein is not particularly limited. For example, when the donor is a non-human, perfusate instream and outstream cannulae may be connected to an organ or tissue for transplantation, and the organ or tissue are isolated after initiating perfusion. When the donor is a human, perfusate instream and outstream cannulae may be connected after isolating an organ or tissue for transplantation, and perfusion is initiated thereafter.

<Mammalian Organ or Tissue for Transplantation>

The third embodiment of the present invention is a mammalian organ or tissue for transplantation, characterized in that said "organ or tissue" is isolated from a mammal, and the blood in said "organ or tissue" is substituted by a perfusate comprising an oxygen carrier and a blood coagulation inhibitor. The terms used in the first embodiment of the present invention will be employed synonymously in the third embodiment, and descriptions therefor will be omitted.

In the third embodiment of the present invention, the method for substituting the blood in the organ or tissue with a perfusate comprising an oxygen carrier and a blood coagulation inhibitor is not particularly limited, and substitution can be e.g. by perfusing the perfusate into the organ or tissue.

Note that the terms used herein are to be employed to describe particular embodiments, and do not intend to limit the invention.

Moreover, the term "comprising" as used herein, unless the content clearly indicates to be understood otherwise, intends the presence of the described items (such as components, steps, elements, and numbers), and does not exclude the presence of other items (such as components, steps, elements, and numbers).

Unless otherwise defined, all terms used herein (including technical and scientific terms) have the same meanings as those broadly recognized by those skilled in the art of the technology to which the present invention belongs. The terms used herein, unless explicitly defined otherwise, are to be construed as having meanings consistent with the meanings herein and in related technical fields, and shall not be construed as having idealized or excessively formal meanings.

Terms such as first and second may be employed to express various elements, and it should be recognized that these elements are not to be limited by these terms. These terms are employed solely for the purpose of discriminating one element from another, and it is for example possible to describe a first element as a second element, and similarly, to describe a second element as a first element without departing from the scope of the present invention.

The present invention will now be more specifically described by Examples. However, the present invention can be embodied by various embodiments, and shall not be construed as being limited to the Examples described herein.

EXAMPLES (1) Preparation of Perfusate
<Preparation of Erythrocytes>

In this Example, a test example employing erythrocytes as oxygen carrier is shown as one embodiment of the present invention. Concentrated human erythrocyte solution was received from the Japanese Red Cross Blood Center upon request for grant of blood that cannot be used for blood transfusion etc. To 50 ml of said concentrated human erythrocyte solution was added 200 ml of L-15 medium (SIGMA), and this was centrifuged at 2000 rpm for 5 minutes. After centrifugation, the supernatant other than the precipitated erythrocyte component was removed, and L-15 medium (SIGMA) was added to a total amount of 250 ml. This operation was repeated twice to prepare the human erythrocytes employed for organ or tissue perfusion.

<Preparation of Perfusates>

The perfusate employed for perfusion was prepared by supplementing L-15 medium (SIGMA) with 10% fetal bovine serum (FBS; Gibco, New York, U.S.), 100 U/ml penicillin, 100 µg/ml streptomycin, 025 µg/ml amphotericin B (nacalai tesque, Kyoto, Japan), 50 µg/ml gentamicin sulfate (Wako, Osaka, Japan), 2 mM L-alanyl/L-glutamine, 50 units/ml heparin (Wako, Osaka, Japan), and 3 µg/ml cyclosporin A.

The perfusate prepared as above is referred to in this Example as an "erythrocyte-nonsupplemented perfusate." Moreover, a perfusate which is the erythrocyte-nonsupplemented perfusate supplemented with human erythrocytes at $5.0 \times 10^{11}$ cells/L is referred to in this Example as an "erythrocyte-supplemented perfusate."

(2) Production of Warm Ischemia Model Rats

Eight-week-old Wistar rats (Japan SLC, Inc.) were placed in a desiccator filled with diethyl ether (Wako) to perform aspiration anesthesia. One hundred microliters of heparin sodium (Wako) solution prepared to have a final concentration of 25000 U/ml was injected to the penile vein of the rats subjected to aspiration anesthesia with a 25 G injection needle (Terumo, Tokyo, Japan) and a 1 ml syringe (Terumo). The injected rats were left for 5 minutes to allow the heparin sodium solution to be systemically delivered, and then sacrificed by cervical dislocation. In this Example, the time point of sacrifice by cervical dislocation was set as the initiation time point of cardiac arrest. The sacrificed rats were left in a cell culture incubator (SANYO, Tokyo, Japan) for 1 hour at room temperature (25° C.)-37° C. The rats after incubation were set in this Example as warm ischemia model rats.

Note that management and operation of rats were performed according to the Guidelines for Experimental Animals of National Institute of Health. Moreover, all experiments were carried out with the permission of Experimental Animals Management Committee at Tokyo University of Science.

(3) Construction of Perfusion Circuit

The schematic diagram of perfusion circuit 1 employed in this Example is shown in FIG. 1. In FIG. 1, the temperature of the perfusate and the amount of oxygen dissolved in the perfusate of the perfusate placed in a first vessel 30 and a second vessel 31 were maintained constant by a simplified animal cell culture device 20 (ABT F, Tokyo, Japan). The perfusate placed in the first vessel 30 was streamed into/out from the organ or tissue subject to perfusion placed in a perfusion vessel for organ immobilization 10 with a peristaltic pump 40 (IWAKI/AGC TECHNO GLASS, Chiba, Japan). The perfusate that streamed out was set up to be retrieved in the second vessel 31. The perfusate retrieved in the second vessel 31 was set up to be returned again to the first vessel 30 with a peristaltic pump 41. A perfusate retrieval port 50 was set up on a part of the tube connecting the organ or tissue and the second vessel 31 in order to collect the perfusate that streamed out from the organ or tissue over time. The above circuit was set as the perfusion circuit employed in this Example.

(4) Investigation of Optimal Erythrocyte Concentration in Perfusate

Eight-week-old Wistar rats (Japan SLC, Inc.) were placed in a desiccator filled with diethyl ether (Wako) to perform aspiration anesthesia One hundred microliters of heparin sodium (Wako) solution prepared to have a final concentration of 25000 U/ml was injected to the inferior vena cava of said rats with a 25 G injection needle (Terumo, Tokyo, Japan) and a 1 ml syringe (Terumo). The injected rats were left for 5 minutes to allow the heparin sodium solution to be systemically delivered, and then sacrificed by cervical dislocation. Immediately after sacrifice, the liver was isolated with the method of (6) described below, and connected to the perfusion circuit to perform perfusion. In other words, the liver of rats immediately after sacrifice is employed instead of the liver of warm ischemia model rats in this investigation of conditions.

The erythrocyte-nonsupplemented perfusate prepared in the method of (1), as well as perfusates having the erythrocyte-nonsupplemented perfusate supplemented with the human erythrocytes prepared in the method of (1) at $0.5 \times 10^{11}$ cells/L, $2.0 \times 10^{11}$ cells/L, and $5.0 \times 10^{11}$ cells/L, respectively, were prepared and employed as perfusates. During perfusion, a simplified animal cell culture device was employed to maintain the temperature of the perfusate at 37° C., and the dissolved oxygen in the perfusate was all maintained at 6.77 mg/L. During perfusion, the liver temperature was maintained at 22° C. by maintaining the L-15 medium inside the perfusion vessel for organ immobilization at 22° C. During perfusion, the flow rate of each perfusate was set at 11 ml/min with a peristaltic pump. During perfusion in the perfusion circuit, the perfusate that streamed out from the liver was sampled every 4 hours from the perfusate retrieval port. The perfusate sampled from the perfusate retrieval port was centrifuged at 1800 rpm for 3 minutes, and the supernatant was retrieved. The ALT activity in the supernatant was measured with Transaminase CII-test Wako (Wako) according to the provided directions for use.

Moreover, the liver after 48 hours after initiation of perfusion was immediately fixed by perfusing with 4% paraformaldehyde-phosphate buffer for 15 minutes. The liver subjected to fixing by perfusion was cut into tissue pieces, and then immersed in 4% paraformaldehyde-phosphate buffer for 24 hours for further fixing Said tissue pieces subjected to fixing by immersion were dehydrated by ethanol solution, penetrated by xylene, and then substituted with paraffin and embedded. The embedded samples were thinly sliced to a thickness of 5 μm, and HE staining was carried out according to conventional means. The stained samples were microscopically examined with Axio Imager A1 (Carl Zeiss) installed with AxioCamMRc5 (Carl Zeiss, Jene, Germany), and images were obtained with Axio Vision Rel. 4.7 (Carl Zeiss).

Comparison of ALT activity obtained in each erythrocyte concentration condition is shown in FIG. 2. As shown in FIG. 2, it was surprisingly found that the increase in ALT activity is human erythrocyte concentration-dependently suppressed. In this Example, it was found that the increase in ALT activity is most suppressed in the grow subjected to perfusion with the perfusate supplemented with human erythrocytes at $5.0 \times 10^{11}$ cells/L.

Moreover, liver tissue images after perfusion under each erythrocyte concentration condition are shown in FIG. 3. As shown in FIG. 3, sinusoidal enlargement and diffuse liver parenchymal cell death were partially seen in the grow subjected to perfusion with the perfusate supplemented with human erythrocytes at $0.5 \times 10^{11}$ cells/L, slight sinusoidal enlargement and partial liver parenchymal cell death were seen in the grow subjected to perfusion with the perfusate supplemented with human erythrocytes at $2.0 \times 10^{11}$ cells/L, and retention of sinusoidal structure almost equivalent to that of the liver immediately after sacrifice and liver parenchymal cell survival were seen in the grow subjected to perfusion with the perfusate supplemented with human erythrocytes at $5.0 \times 10^{11}$ cells/L. In other words, erythrocyte concentration-dependent suppression of liver tissue disorder was seen, and it was found in this Example that the grow subjected to perfusion with the perfusate supplemented with human erythrocytes at $5.0 \times 10^{11}$ cells/L was the most suppressed in tissue disorder.

In other words, it was found that by performing perfusion of an organ or tissue for transplantation with the perfusate supplemented with human erythrocytes at $5.0 \times 10^{11}$ cells/L, organ or tissue disorder after isolation can be most significantly suppressed, thereby enabling a long-term preservation while maintaining the organ or tissue function.

(5) Investigation of Optimal Temperature Condition During Perfusion

Eight-week-old Wistar rats (Japan SLC, Inc.) were placed in a desiccator filled with diethyl ether (Wako) to perform aspiration anesthesia One hundred microliters of heparin sodium (Wako) solution prepared to have a final concentration of 25000 U/ml was injected to the inferior vena cava of said rats with a 25 G injection needle (Terumo, Tokyo, Japan) and a 1 ml syringe (Terumo). The injected rats were left for 5 minutes to allow the heparin sodium solution to be systemically delivered, and then sacrificed by cervical dislocation. Immediately after sacrifice, the liver was isolated with the method of (6) described below, and connected to the perfusion circuit to perform perfusion. In other words, the liver of rats immediately after sacrifice is employed instead of the liver of warm ischemia model rats in this investigation of conditions.

The perfusate employed was the erythrocyte-supplemented perfusate prepared in the method described in (1). Dining perfusion, a simplified animal cell culture device was employed to maintain the temperature of the perfusate at 37° C., and the dissolved oxygen in the perfusate was all maintained at 6.77 mg/L. During perfusion, the liver temperature was maintained at each temperature by maintaining the L-15 medium inside the perfusion vessel for organ immobilization at 37° C., 33° C., or 22° C. During perfusion, the flow rate of the erythrocyte-supplemented perfusate was set at 11 ml/min with a peristaltic pump. During perfusion in the perfusion circuit, the erythrocyte-supplemented perfusate that streamed out from the liver was sampled every 4 hours from the perfusate retrieval port. The perfusate sampled from the perfusate retrieval port was centrifuged at 1800 rpm for 3 minutes, and the supernatant was retrieved. The ALT activity in the perfusate supernatant was measured with Transaminase CII-test Wako (Wako) according to the provided directions for use.

Fixing was performed after 20 hours from initiation of perfusion for the liver perfused at 37° C., after 32 hours from initiation of perfusion for the liver perfused at 33° C., and after 48 hours from initiation of perfusion for the liver perfused at 22° C. Fixing was performed by perfusing the liver with 4% paraformaldehyde-phosphate buffer for 15 minutes. The liver subjected to fixing by perfusion was cut into tissue pieces, and then immersed in 4% paraformaldehyde-phosphate buffer for 24 hours for further fixing. Said tissue pieces subjected to fixing by immersion were dehydrated by ethanol solution, penetrated by xylene, and then substituted with paraffin and embedded. The embedded samples were thinly sliced to a thickness of 5 µm, and HE staining was carried out according to conventional means. The stained samples were microscopically examined with Axio Imager A1 (Carl Zeiss) installed with AxioCamMRc5 (Carl Zeiss, Jene, Germany), and images were obtained with Axio Vision Rel. 4.7 (Carl Zeiss).

Comparison of ALT activity obtained in each temperature condition is shown in FIG. 4. As shown in FIG. 4, it was surprisingly found that the increase in ALT activity is most suppressed in the group in which perfusion was performed while maintaining the liver at 22° C.

Moreover, liver tissue images after perfusion under each temperature condition are shown in FIG. 5. As shown in FIG. 5, when perfusion was performed at 37° C., liver parenchymal cell necrosis and disruption of sinusoidal structure were observed at a time point 20 hours after initiation of perfusion. Moreover, when perfusion was performed at 33° C., even though tissue structure maintenance effect was observed for a longer term, liver parenchymal cell necrosis and disruption of sinusoidal structure were observed at a time point 32 hours after initiation of perfusion. However, when perfusion was performed at 22° C., it was found that sinusoidal structure almost equivalent to that of the liver immediately after sacrifice were observed, and the intrahepatic vascular plexus structure was also highly preserved even at a time point 48 hours after initiation of perfusion.

In other words, it was found that by performing perfusion while maintaining an organ or tissue for transplantation at 22° C., organ or tissue disorder can be most significantly suppress, thereby enabling a long-term preservation while maintaining the organ or tissue function.

(6) Liver Perfusion with Erythrocyte-Supplemented Perfusate

<Washing of Warm Ischemia Model Rat Liver and Liver Isolation>

Warm ischemia model rats produced by the method described in (2) were employed for the experiment. The abdomen of warm ischemia model rat was incised, the subhepatic inferior vena cava was stripped to the left renal vein bifurcation, and the right renal vein, the left renal vein, and the lumbar vein were each ligated with silk surgical suture No. 7 (Natume). Silk surgical suture No. 4 (Natume) was passed through the subhepatic inferior vena cava caudal to the left renal vein bifurcation to make one ligation loop. The portal vein was stripped from the connective tissue, and silk surgical suture No. 7 (Natume) was passed through in the order of the hepatic artery proper, the pyloric vein, and the splenic vein and ligated. Two silk surgical sutures No. 4 (Natume) was passed through the portal vein with an interval to make two ligation loops. The temperature of the erythrocyte-supplemented perfusate was maintained at 37° C. and the dissolved oxygen in the erythrocyte-supplemented perfusate was maintained at 6.77 mg/L by a simplified animal cell culture device. The erythrocyte-supplemented perfusate was streamed through the perfusate instream cannula at 11 ml/min with a peristaltic pump, and then the portal vein was halved and said perfusate instream cannula was inserted. Next, the subhepatic inferior vena cava was immediately transected below the ligation loop, and the erythrocyte-supplemented perfusate was allowed to stream out from the transacted site. The two ligation loops of the portal vein were ligated to immobilize the perfusate instream cannula to the portal vein, and the insertion site of the perfusate instream cannula was immobilized with an appropriate amount of Aron Alpha A (Daiichi Sankyo, Tokyo, Japan).

The costal bone was incised, and silk surgical suture No. 4 (Natume) was passed through the suprahepatic inferior vena cava to make two ligation loops. After the right atrium was halved, the loop set up on the subhepatic inferior vena cava was ligated. The perfusate outstream cannula was inserted into the halved right atrium portion, the two ligation loops of the suprahepatic inferior vena cava were ligated to immobilize the perfusate outstream cannula, and the ligation site and the insertion site of the perfusate outstream cannula were immobilized with Aron Alpha A (Daiichi Sankyo). The common bile duct was halved, a bile outstream cannula was inserted, and immobilized with Aron Alpha A (Daiichi Sankyo). The diaphragm was exposed, and the left and right phrenic artery/veins were ligated with silk surgical suture No. 7 (Natume). After the organs and connective tissue surrounding the liver were resected, the liver was detached from the dorsal with the costal bone and the diaphragm still linked to the liver, and isolated.

The isolated liver was carried to the perfusion vessel for organ immobilization, the entire liver was suspended by immobilizing the costal bone to a fixture attached to the perfusion vessel for organ immobilization, and L-15 medium was filled inside the perfusion vessel for organ immobilization. The liver was in a suspended state with the costal bone and the diaphragm and floated in L-15 medium.

The temperature of the floating liver was maintained at 22° C. by maintaining the L-15 medium inside the perfusion vessel for organ immobilization at 22° C.

The inside of liver blood vessels were washed for 100 minutes from when the erythrocyte-supplemented perfusate was streamed into the liver. The schematic diagram of a device for washing the liver in this Example is shown in FIG. 6. In FIG. 6, the isolated liver was immobilized to a perfusion vessel for organ immobilization 11. The erythrocyte-supplemented perfusate placed in a first vessel 32 was streamed into the liver via the perfusate instream cannula, and streamed out of the suprahepatic inferior vena cava via the perfusate outstream cannula. The erythrocyte-supplemented perfusate streamed out of the suprahepatic inferior vena cava was removed without circulating to the first vessel 32, and all retrieved in a second vessel 33. During said 100-minute washing, the erythrocyte-supplemented perfusate that streamed out from the liver was sampled every 10 minutes from a perfusate retrieval port 51 that was set up on a part of the tube connected to the perfusate outstream cannula.

<Perfusion in Perfusion Circuit>

After said 100-minute liver washing, the liver was connected to the perfusion circuit described in (3). The temperature of the erythrocyte-supplemented perfusate was maintained at 37° C. and the dissolved oxygen in the erythrocyte-supplemented perfusate was maintained at 6.77 mg/L by a simplified animal cell culture device. During perfusion, the temperature of the floating liver was maintained at 22° C. by maintaining the L-15 medium inside the perfusion vessel for organ immobilization at 22° C. Said erythrocyte-supplemented perfusate was streamed into the liver connected to the perfusion circuit at 11 ml/min with a peristaltic pump (IWAKI/AGC TECHNO GLASS, Chiba, Japan). During perfusion in the perfusion circuit, the erythrocyte-supplemented perfusate that streamed out from the liver was sampled every 4 hours from the perfusate retrieval port.

(7) Liver Perfusion with Erythrocyte-Nonsupplemented Perfusate

Steps similar to those in (6) were performed with an erythrocyte-nonsupplemented perfusate.

(8) Analysis of Liver Tissue Disorder

<Analysis of Liver Disorder Enzyme (ALT) Activity>

In the experiments of (6) and (7), the perfusates sampled from the perfusate retrieval port during washing inside blood vessels and perfusion in the perfusion circuit were centrifuged at 1800 rpm for 3 minutes, and the supernatants were retrieved. The ALT activity in the perfusate supernatant was measured with Transaminase CII-test Wako (Wako) according to the provided directions for use.

For results up to 48 hours after initiation of perfusion, comparison of the results obtained from the group employing an erythrocyte-supplemented perfusate and the group employing an erythrocyte-nonsupplemented perfusate is shown in FIG. 7. A magnified view of the measurement graph of the ALT activity in the perfusate during liver washing before initiation of perfusion by the perfusion circuit (before 0 minutes) within FIG. 7 is shown in FIG. 8. As shown in FIG. 7, the ALT activity when perfusion was performed with an erythrocyte-nonsupplemented perfusate reached 57 units/Liver at 48 hours after initiation of perfusion by the perfusion circuit. On the other hand, the ALT activity when perfusion was performed with an erythrocyte-supplemented perfusate remained at 32 units/Liver at 48 hours after initiation of perfusion by the perfusion circuit. Moreover, as shown in FIG. 8, in regards to the ALT activity of the perfusates that streamed out from the liver sampled during the 100-minute washing of inside blood vessels, the group employing an erythrocyte-nonsupplemented perfusate reached 17 units/Liver, whereas the group employing an erythrocyte-supplemented perfusate remained at 12 units/ Liver.

From the above results, it was found that a clear liver tissue disorder suppression effect is seen with the group that was performed perfusion with an erythrocyte-supplemented perfusate compared to the group that was performed perfusion with an erythrocyte-nonsupplemented perfusate.

<Histological Analysis>

In the experiments of (6) and (7), the liver after 48 hours of perfusion was immediately fixed by perfusing with 4% paraformaldehyde-phosphate buffer for 15 minutes. The liver subjected to fixing by perfusion was cut into tissue pieces, and then immersed in 4% paraformaldehyde-phosphate buffer for 24 hours for further fixing Said tissue pieces subjected to fixing by immersion were dehydrated by ethanol solution, penetrated by xylene, and then substituted with paraffin and embedded. The embedded samples were thinly sliced to a thickness of 5 µm, and HE staining was carried out according to conventional means. The stained samples were microscopically examined with Axio Imager A1 (Carl Zeiss) installed with AxioCamMRc5 (Carl Zeiss, Jene, Germany), and images were obtained with Axio Vision Rel. 4.7 (Carl Zeiss).

HE staining images of the liver perfused with an erythrocyte-supplemented perfusate are shown in FIG. 9, and HE staining images of the liver perfused with an erythrocyte-nonsupplemented perfusate is shown in FIG. 10. FIGS. 9 and 10 each show magnified images of different portions of one image of one liver section at 1× to 40× magnifications.

In FIGS. 9 and 10, tissue images from 10× to 40× magnifications are magnified views of the portion surrounded by a box in the tissue image at 1× magnification. Tissue images at 40× magnification in FIGS. 9 and 10 each show the magnified view of the portal area, the hepatic parenchyma, and the central vein. As shown in FIG. 9, when perfusion was performed with an erythrocyte-supplemented perfusate, even though a certain extent of sinusoidal enlargement is seen, many liver parenchymal cell survival is seen in the liver tissue at 48 hours after initiation of perfusion by the perfusion circuit. On the other hand, as shown in FIG. 10, when perfusion was performed with an erythrocyte-nonsupplemented perfusate, normal staining image is only seen around the portal area, and diffuse necrosis image and enlargement of the sinusoidal region were observed in the liver tissue at 48 hours after initiation of perfusion by the perfusion circuit.

From the above results, it was found that reduction in diffuse necrosis region of the liver and sinusoidal enlargement suppression effect were seen when perfusion was performed with an erythrocyte-supplemented perfusate compared to when perfusion was performed with an erythrocyte-nonsupplemented perfusate.

<Measurement of Albumin Synthesis Amount 1>

In the experiments of (6) and (7), the perfusates collected over time from the perfusate retrieval port were centrifuged at 1800 rpm for 3 minutes to retrieve the supernatants. The measurement of albumin concentration in the perfusate supernatant was measured by FT TSA with Rat Albumin FT ISA KIT (shibayagi, Gunma, Japan) according to the provided directions for use.

The transition of albumin concentration in the perfusate up to 48 hours from initiation of perfusion in the perfusion circuit is shown in FIG. 11. As shown in FIG. 11, it was shown that albumin synthesis ability of the liver is maintained significantly high when perfusion was performed with an erythrocyte-supplemented perfusate compared to when perfusion was performed with an erythrocyte-nonsupplemented perfusate.

<Measurement of Albumin Synthesis Amount 2>

In the experiments of (6) and (7), the perfusates collected over time from the perfusate retrieval port were centrifuged at 1800 rpm for 3 minutes to retrieve the supernatants. The measurement of albumin concentration in the perfusate supernatant was measured by ELISA with rat albumin quantitation kit (Bethyl, Montgomery, USA). The primary antibody Sheep anti-Rat Albumin Antibody Affinity Purified (1:200) was solid-phased on a 96-well multiplate, blocked with 1% BSA, and then samples were added. After antibody reaction with Sheep anti-Rat Albumin Antibody HRP Conjugated (1:30000) as the secondary antibody, color was developed by TMB (Bethyl) and absorbance was detected with VersaMax (Molecular Devices) to quantitatively measure albumin concentration.

The transition of albumin concentration in the perfusate up to 48 hours from initiation of perfusion in the perfusion circuit is shown in FIG. 12. As shown in FIG. 12, the amount of albumin synthesized during the 48-hour perfusion reached 10.3±1.3 mg/mL when perfusion was performed with an erythrocyte-supplemented perfusate, whereas the amount of albumin synthesized during the 48-hour perfusion remained at 3.5±1.0 mg/mL when perfusion was performed with an erythrocyte-nonsupplemented perfusate. In other words, it was shown that albumin synthesis ability of the liver is maintained significantly high when perfusion was performed with an erythrocyte-supplemented perfusate compared to when perfusion was performed with an erythrocyte-nonsupplemented perfusate.

<Measurement of Urea Synthesis Ability by Ammonia Loading Test>

In the experiments of (6) and (7), Krebs-Henseleit Buffer was perfused to the liver after the 48-hour perfusion from the portal vein at a speed of 11 ml/min for 2 hours to wash the blood and the perfusate inside the organ. Next, Krebs-Henseleit Buffer supplemented with 1 mM omithine hydrochloride and 1 mM ammonium chloride was perfused at 11 ml/min for 30 minutes to perform an ammonia loading test, and the Krebs-Henseleit Buffer streaming out from the suprahepatic inferior vena cava was collected over time. The liver which was isolated immediately after sacrifice with the method described in (6) and then connected to the perfusion circuit was also subjected to the ammonia loading test similarly to above, and the Krebs-Henseleit Buffer streaming out from the suprahepatic inferior vena cava was successively collected. At the end of the 30-minute ammonia loading test, Krebs-Henseleit Buffer was delivered again to wash the solution inside the organ, and Krebs-Henseleit Buffer was collected over time. The collected Krebs-Henseleit Buffer was centrifuged at 1800 rpm for 3 minutes to retrieve the supernatant, and the amount of urea was measured with F-kit urea/ammonia (JK International, Tokyo, Japan) according to the provided specification.

The temporal change in the amount of urea comprised in the collected Krebs-Henseleit Buffer is shown in FIG. 13. As shown in FIG. 13, it was shown that the amount of urea synthesized by ammonia loading is maintained significantly high when perfusion was performed with an erythrocyte-supplemented perfusate compared to when perfusion was performed with an erythrocyte-nonsupplemented perfusate, and about 60% of the amount of urea synthesized is maintained even when compared to the liver immediately after sacrifice.

In other words, from the results of measurement of albumin synthesis amount and of urea synthesis ability by ammonia loading test, it was found that liver metabolism function is maintained significantly high when perfusion was performed with an erythrocyte-supplemented perfusate compared to when perfusion was performed with an erythrocyte-nonsupplemented perfusate.

<Analysis of Intrahepatic Vascular Plexus>

In the experiments of (6) and (7), the liver after the 48-hour perfusion was immediately perfused with saline to wash the erythrocytes or the perfusate in the organ. After washing, this was perfused with 25 ml of gelatin labeled with FITC, then placed under freezing temperature to solidify the gelatin in the vascular plexus in the organ. After the gelatin is solidified, the organ was immersed in 0.5% paraformaldehyde-phosphate buffer and fixed. This was then freeze-embedded with OCT compound. The frozen blocks produced were cut into sections at a thickness of 100 μm, treated with sodium deoxycholate, and then fixed with 4% paraformaldehyde-phosphate buffer comprising Hoechst. The liver which was isolated immediately after sacrifice with the method described in (6) was also subjected to a treatment similar to the above. After mounting with a mounting agent, images were obtained by Z-stack with a cofocal laser microscope LSM780 (Carl Zeiss).

Fluorescence images for each liver section are shown in FIG. 14. As shown in FIG. 14, it was found that there is only a little leakage of the fluorescent dye outside the blood vessel and the blood vessel structure is highly maintained when perfusion was performed with an erythrocyte-supplemented perfusate compared to when perfusion was performed with an erythrocyte-nonsupplemented perfusate.

In other words, from the analysis of the intrahepatic vascular plexus, it was found that the liver blood vessel structure is restored to a state close to that of the liver immediately after sacrifice when perfusion was performed with an erythrocyte-supplemented perfusate compared to when perfusion was performed with an erythrocyte-nonsupplemented perfusate.

(9) Engraftment Evaluation of Ischemic Organ by Heterotopic Liver Transplantation <Heterotopic Liver Transplantation>

Warm ischemia model rats produced with a method similar to the method described in (2) except that they were left at room temperature with a cell culture incubator for 90 minutes after cardiac arrest were employed as donors of heterotopic liver transplantation. Said warm ischemia model rats were employed for isolation and perfusion of the liver with the method described in (6). After perfusion, the portal vein cannula was removed, a new tube for perfusion was connected, and perfusion was performed with 500 ml of a perfusate comprising erythrocytes ($5.0 \times 10^{11}$ cells/L) that was not supplemented with heparin. During perfusion, the recipient 13 week-old Wistar rats (SLC) were transferred to a desiccator filled with diethyl ether (Wako) to perform aspiration anesthesia. The anesthetic environment was set at 4% isoflurane concentration, and abdominal incision of rats was performed. The right renal artery was exposed, stripped from the right renal vein, the blood flow of these were cut off with a clip, and then transacted. A cuff was installed at the transected site. The subhepatic inferior vena cava was half-clamped, the right renal vein was transected, and the right kidney was isolated. The donor liver was set up at the surgery site without ceasing perfusion, and end-to-side anastomosis of the subhepatic inferior vena cava thereof to the right renal vein the recipient was performed Next, anastomosis of the hepatic artery of the donor liver to the right renal artery of the recipient was performed by cuffing After anastomosis, reperfusion of the hepatic artery and the subhepatic inferior vena cava was performed, the cannula connected to the portal vein was removed, and then end-to-side anastomosis of the portal vein of the donor liver to the portal vein of the recipient was performed, and reperfusion of the portal vein after anastomosis was performed Two milliliters of transfusion was injected from the penile vein. A bile duct stent was inserted into the jejunum, immobilized by anastomosis, and the peritoneum and the skin were sutured to close the abdomen. The schematic diagram of heterotopic liver transplantation in this Example is shown in FIG. 15.

<Engraftment Evaluation of Ischemic Organ by Heterotopic Liver Transplantation>

In order to clarify that an organ or tissue perfused by the method of the present invention can be employed for transplantation, engraftment evaluation of organs by heterotopic liver transplantation was performed with the following Groups 1-3.

Group 1: Heterotopic liver transplantation was performed with livers perfused with the method of the present invention using the method described above (also referred to herein as the erythrocyte-supplemented group).

Group 2: Heterotopic liver transplantation was performed with liver of rats after a 90-minute warm ischemic state (i.e., liver of rats with 90 minutes of incubation by a cell culture incubator in the warm ischemia model rat production method described in (2)) after penetration preservation under cool temperature employing UW solution (Viaspan, Astellas Parma Inc., Japan) as the organ preservation solution for 100 minutes (also referred to herein as the UW preservation group). Penetration preservation under cool temperature employing UW solution as the preservation solution is a preservation method of organ for transplantation that is commonly performed in current transplantation medical care.

Group 3: Heterotopic liver transplantation was performed similarly to Group 1, except that livers were perfused with an erythrocyte-nonsupplemented perfusate (also referred to herein as the erythrocyte-nonsupplemented group).

Rat survival rate up to transplantation Day 7 for each group is shown in FIG. 16.

As shown in FIG. 16, rat survival rate at 7 days after transplantation was 40% for the UW preservation group, and rat survival rate at 7 days after transplantation was 60% for the erythrocyte-nonsupplemented group. On the other hand, surprisingly, rat survival rate at 7 days after transplantation was 100% for the erythrocyte-supplemented group. It was also shown from the appearance observation of the transplant organ that the transplanted organ was maintained by the host blood flow in the erythrocyte-supplemented group and was engrafted to the living body.

Further, tissue analysis by HE staining was performed for individuals that have died during follow-up observation. As a result, disappearance of liver parenchymal cells and fibrosing of tissue, as well as lymphocyte invasion were confirmed with the UW preservation group, and retention of erythrocytes or portions without nucleus staining were confirmed with the erythrocyte-nonsupplemented group, suggesting the possibility that tissue necrosis have occurred. On the other hand, in the erythrocyte-supplemented group, although enlargement of Glisson's capsule in the portal area was partially seen in the transplant organ from the results of tissue analysis at 7 days after transplantation, survival cells and sinusoidal structure similar to that of a living liver were observed in the tissue image, showing engraftment of the transplant liver. The results of these tissue analyses are shown in FIG. 17.

In other words, according to the method of the present invention, it was shown that an organ that has once come to be in a warm ischemic state can be maintained at and/or restored to a safely transplantable state. Since it was conventionally thought that it is extremely difficult to employ an organ that has once come to be in a warm ischemic state for transplantation, the results of this Example can be said to be surprising.

(10) Analysis of Physiologic Liver Function of Transplant Organ by Hepatic Resection/Hepatic Portal VEIN LIGATION <Hepatic Resection/Hepatic Portal Vein Ligation of Rat Subjected to Heterotopic Liver Transplantation>

Heterotopic liver transplantation was performed with the method described in (9), and individuals after 7 days after transplantation were transferred to a desiccator filled with diethyl ether (Wako) to perform aspiration anesthesia. The anesthetic environment was set at 4% isoflurane concentration, and abdominal incision of rats was performed. The left lobe, the left middle lobe, and right middle lobe of the host liver were ligated to the respective lobulation site with silk surgical suture No. 4, and resected after the blood flow was ceased. The portal vein leading to the host liver was then ligated with silk surgical suture No. 4, and the peritoneum and the skin were sutured to close the abdomen. The schematic diagram of hepatic portal vein ligation in this Example is shown in FIG. 18.

<Analysis of Physiologic Liver Function in Transplant Organ>

In order to clarify that the transplant organ has normal liver function, the liver function was reduced by partial hepatic resection of the host liver and ligation of the portal vein leading to the host liver, and it was evaluated whether surrogation of function by the transplant organ was possible. In the UW preservation group that was performed transplantation with conventional organ preservation technology and the erythrocyte-nonsupplemented group that was performed perfusion of the transplant organ without supplementing erythrocytes, death was confirmed in all cases after the host liver function was reduced (FIG. 19). In contrast, in the erythrocyte-supplemented group that was performed perfusion of the transplant organ with the method of the present invention, 5 survival cases out of 5 cases were observed (FIG. 19). From the above results, it became clear that the organ that was performed perfusion with the method of the present invention maintains the organ function necessary for survival of individuals.

Moreover, in order to evaluate the in vivo function of the transplant liver, hepatic regeneration capacity was analyzed in the erythrocyte-supplemented group. The mean value of the host liver weight at 7 days after transplantation (before partial hepatic resection) was 9.27 g, and the mean value of the transplant liver was 3.386 g. The mean value of the host liver weight decreased to 3.26 g by 70% partial hepatic resection. After the follow-up observation of 7 days after partial hepatic resection of the host liver, the host organ and the transplant organ were both isolated and weighed. As a result, the mean value of the host liver weight was not changed much at 3.28 g, whereas the mean value of the transplant liver had increased to 8.24 g (FIG. 20).

From the above results, it was shown that the method of the present invention is a technology that not only enables an organ that has once come to be in a warm ischemic state to be utilized in transplantation, but a technology that may also resuscitate it to an organ that has physiological functions necessary for survival.

Further, in order to determine whether the increase in the hepatic weight of the transplant liver had gone through normal hepatic regeneration process, tissue analysis by HE staining as well as albumin and Brd-U expression analysis by immunostaining were performed on the liver after 1 week after partial hepatic resection of the host liver and portal vein ligation. As shown in FIGS. 21 and 22, in the transplant liver before partial resection of the host liver, although tissue structure equivalent to that of normal liver tissue is seen, expression of albumin was almost undetected. However, structural change in the hepatic cord of the transplant liver and the enlargement of the sinusoidal structure were confirmed with the reduction of liver function of the host liver. It was also confirmed that albumin production amount was clearly increased in the transplant liver at day 7 after partial resection of the host liver. Further, liver regeneration by cell proliferation was shown due to the fact that Brd-U positive cells (i.e. cells undergoing cell division) accounted for 47.7% of total number of cells in the transplant liver at day 7 after partial resection of the host liver.

From the above results, it was found that when the liver perfused by the method of the present invention is employed for transplantation, the transplanted liver shows restoration of normal liver function and increase in weight in correspondence with reduction of liver function of the host liver.

For the experiment data, Pearson's product-moment correlation coefficient was analyzed with IBM SPSS Statistics Base (SPSS Inc., Tokyo, Japan). The statistical significant difference of each experiment data was analyzed with impaired student's-t test. Analysis was performed with Common Gateway Interface Program (twk, Saint John's University, Minnesota, USA).

(11) Conclusion

From the above results, it was surprisingly found that extremely high tissue disorder suppression effect is seen when an organ for transplantation was perfused with an erythrocyte-supplemented perfusate. In other words, it was found that by perfusing an organ or tissue for transplantation with an erythrocyte-supplemented perfusate, organ or tissue disorder after isolation can be significantly suppressed, thereby enabling a long-term maintenance while maintaining the organ or tissue function.

It was also found that by perfusing a liver that has come to be in a warm ischemic state due to cardiac arrest with an erythrocyte-supplemented perfusate, development of liver disorder can be suppressed, and liver parenchymal cells and sinusoidal structure can be restored to a state close to the liver immediately after cardiac arrest.

Further, when the liver perfused with an erythrocyte-supplemented perfusate was employed for transplantation, extremely high engraftment rate in the host was shown compared to the liver that was preserved with conventional organ preservation technology or when the liver perfused with an erythrocyte-nonsupplemented perfusate was employed for transplantation. It was also shown that when the liver perfused with an erythrocyte-supplemented perfusate was employed for transplantation, it may act as a liver having normal function and structure.

From these results, it was shown that the present invention is extremely useful as a technology for maintaining and/or restoration an organ or tissue from a cardiac arrest patient at/to a level compatible for transplantation. It goes without saying that the present invention may be employed usefully not only for an organ or tissue from a cardiac arrest patient but also for organ or tissues in various states such as e.g. an organ from a brain-dead patient.

DESCRIPTION OF SYMBOLS

1: Perfusion circuit;
10, 11: Perfusion vessels for organ immobilization;
20: Simplified animal cell culture device;
30, 31, 32, 33: Vessels;
40, 41: Peristaltic pumps; and
50, 51: Perfusate retrieval ports

The invention claimed is:

1. A method to restore and maintain mammalian liver function for transplantation that employs perfusion by a perfusate, comprising each of the following steps of:
   a) connecting a perfusate instream cannula for streaming said perfusate into the liver,
   b) connecting a perfusate outstream cannula for streaming said perfusate out from said liver, and
   c) perfusing a perfusate comprising $0.5 \times 10^{11}$-$50.0 \times 10^{11}$ cells/L of erythrocytes and a blood coagulation inhibitor into said liver while maintaining the temperature of the liver at 20° C.-25° C.

2. The method according to claim 1, wherein the perfusate in said step (c) is circulated.

3. The method according to claim 2, characterized in that it further comprises a further subsequent step of:
   d) before said step (c), perfusing said liver with a perfusate comprising an oxygen carrier and a blood coagulation inhibitor to wash said liver, and then removing the perfusate employed for said washing.

4. The method according to claim 1, characterized in that in said step (c), said liver is isolated together with a second organ or tissue that is continuous in vivo to said liver, and
perfusion is performed with said liver in a suspended state by immobilizing said second organ or tissue.

5. The method according to claim 4, characterized in that in said step (c), said organ or tissue is immersed in a liquid so that at least a part thereof receives buoyancy.

6. The method according to claim 1, characterized in that said blood coagulation inhibitor is heparin.

* * * * *